(12) United States Patent
Chen et al.

(10) Patent No.: US 12,005,221 B2
(45) Date of Patent: Jun. 11, 2024

(54) CRYO FORMULATION-BASED MICRONEEDLE DEVICE FOR TRANSDERMAL DELIVERY OF BIOACTIVE THERAPEUTIC AGENTS AND CANCER IMMUNOTHERAPY USING A CRYO-MICRONEEDLE PATCH

(71) Applicant: City University of Hong Kong, Kowloon (HK)

(72) Inventors: Peng Chen, Kowloon (HK); Chenjie Xu, Kowloon (HK); Hao Chang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 251 days.

(21) Appl. No.: 17/443,507

(22) Filed: Jul. 27, 2021

(65) Prior Publication Data

US 2022/0062606 A1 Mar. 3, 2022

Related U.S. Application Data

(60) Provisional application No. 63/071,491, filed on Aug. 28, 2020.

(51) Int. Cl.
*A61M 37/00* (2006.01)
*A61K 35/15* (2015.01)
(Continued)

(52) U.S. Cl.
CPC ......... *A61M 37/0015* (2013.01); *A61K 35/15* (2013.01); *B29C 39/003* (2013.01);
(Continued)

(58) Field of Classification Search
CPC ...... A61M 37/0015; A61M 2037/0023; A61M 2037/0053; A61M 2037/0061;
(Continued)

(56) References Cited

U.S. PATENT DOCUMENTS

2002/0091357 A1* 7/2002 Trautman ............. A61B 17/205
606/186
2005/0244385 A1* 11/2005 Brittingham ............ A61P 37/04
604/500
(Continued)

FOREIGN PATENT DOCUMENTS

WO 2015132568 9/2015

OTHER PUBLICATIONS

S. K. Wculek, F. J. Cueto, A. M. Mujal, I. Melero, M. F. Krummel, D. Sancho, Nat Rev Immunol 2020, 20, 7.
(Continued)

*Primary Examiner* — Amber R Stiles
(74) *Attorney, Agent, or Firm* — Renner, Kenner, Greive, Bobak, Taylor & Weber

(57) ABSTRACT

A cryo formulation-based microneedle device for transdermal delivery of bioactive therapeutic agents. The microneedle device includes: one or more microneedle patches each including an array of miniaturized needles, wherein each miniaturized needle defining a base end and a tip; and a substrate to which the base end of the array of miniaturized needles is attached or integrated thereto; wherein the microneedle patch is in a cryo status; wherein each of the one or more microneedle patch is adapted to be applied on a skin surface, in which the miniaturized needles penetrates into skin; and wherein the miniaturized needles is further arranged to melt so as to release one or more bioactive therapeutic agents into the skin to achieve a targeted therapeutic effect.

17 Claims, 18 Drawing Sheets
(2 of 18 Drawing Sheet(s) Filed in Color)

(51) Int. Cl.
    *B29C 39/00*     (2006.01)
    *B29C 39/02*     (2006.01)
    *B29C 39/26*     (2006.01)
    *B29K 105/00*     (2006.01)
    *B29L 31/00*     (2006.01)

(52) U.S. Cl.
    CPC ............ *B29C 39/026* (2013.01); *B29C 39/26* (2013.01); *A61M 2037/0023* (2013.01); *A61M 2037/0053* (2013.01); *A61M 2037/0061* (2013.01); *B29K 2105/0035* (2013.01); *B29K 2105/0073* (2013.01); *B29K 2883/00* (2013.01); *B29K 2905/00* (2013.01); *B29L 2031/7544* (2013.01)

(58) Field of Classification Search
    CPC ........... A61M 2037/0046; A61K 35/15; B29C 39/003; B29C 39/026; B29C 39/26; B29C 39/38; B29K 2105/0035; B29K 2105/0073; B29K 2883/00; B29K 2905/00; B29L 2031/7544; B29L 2031/756
    See application file for complete search history.

(56) References Cited

U.S. PATENT DOCUMENTS

| | | | |
|---|---|---|---|
| 2010/0114348 A1* | 5/2010 | Boyden | G16H 50/50 700/109 |
| 2017/0050010 A1* | 2/2017 | McAllister | B33Y 80/00 |
| 2019/0046479 A1* | 2/2019 | Pathak | A61K 9/1641 |
| 2019/0083703 A1* | 3/2019 | Gu | A61K 31/728 |
| 2023/0033564 A1* | 2/2023 | Xu | A61K 9/0021 |
| 2023/0038697 A1* | 2/2023 | Xu | A61F 9/0008 |

OTHER PUBLICATIONS

R. A. Belderbos, J. Aerts, H. Vroman, Mol Ther Oncolytics 2019, 13, 67.
W. W. van Willigen, M. Bloemendal, W. R. Gerritsen, G. Schreibelt, I. J. M. de Vries, K. F. Bol, Front Immunol 2018, 9, 2265.
T. Wieder, T. Eigentler, E. Brenner, M. Rocken, J Allergy Clin Immunol 2018, 142, 1403.
X. Han, H. Li, D. Zhou, Z. Chen, Z. Gu, Acc Chem Res 2020, 53, 2521.
M. Saxena, S. Balan, V. Roudko, N. Bhardwaj, Nat Biomed Eng 2018, 2, 341.
J. Gao, N. Navai, O. Alhalabi, A. Siefker-Radtke, M. T. Campbell, R. S. Tidwell, C. C. Guo, A. M. Kamat, S. F. Matin, J. C. Araujo, A. Y. Shah, P. Msaouel, P. Corn, J. Wang, J. N. Papadopoulos, S. S. Yadav, J. M. Blando, F. Duan, S. Basu, W. Liu, Y. Shen, Y. Zhang, M. D. Macaluso, Y. Wang, J. Chen, J. Zhang, A. Futreal, C. Dinney, J. P. Allison, S. Goswami, P. Sharma, Nat Med 2020, DOI: 10.1038/s41591-020-1086-y.
F. Dammeijer, M. van Gulijk, E. E. Mulder, M. Lukkes, L. Klaase, T. van den Bosch, M. van Nimwegen, S. P. Lau, K. Latupeirissa, S. Schetters, Y. van Kooyk, L. Boon, A. Moyaart, Y. M. Mueller, P. D. Katsikis, A. M. Eggermont, H. Vroman, R. Stadhouders, R. W. Hendriks, J. V. Thusen, D. J. Grunhagen, C. Verhoef, T. van Hall, J. G. Aerts, Cancer Cell 2020, 38, 685.
J. Larkin, V. Chiarion-Sileni, R. Gonzalez, J. J. Grob, P. Rutkowski, C. D. Lao, C. L. Cowey, D. Schadendorf, J. Wagstaff, R. Dummer, P. F. Ferrucci, M. Smylie, D. Hogg, A. Hill, I. Marquez-Rodas, J. Haanen, M. Guidoboni, M. Maio, P. Schoffski, M. S. Carlino, C. Lebbe, G. McArthur, P. A. Ascierto, G. A. Daniels, G. V. Long, L. Bastholt, J. I. Rizzo, A. Balogh, A. Moshyk, F. S. Hodi, J. D. Wolchok, N Engl J Med 2019, 381, 1535.
H. Chang, M. J. Zheng, S. W. T. Chew, C. J. Xu, Advanced Materials Technologies 2020, 5, 1900552.
A. Than, C. Liu, H. Chang, P. K. Duong, C. M. G. Cheung, C. Xu, X. Wang, P. Chen, Nat Commun 2018, 9, 4433.
H. Chang, M. Zheng, X. Yu, A. Than, R. Z. Seeni, R. Kang, J. Tian, D. P. Khanh, L. Liu, P. Chen, C. Xu, Adv Mater 2017, 29, 1702243.
K. T. M. Tran, T. D. Gavitt, N. J. Farrell, E. J. Curry, A. B. Mara, A. Patel, L. Brown, S. Kilpatrick, R. Piotrowska, N. Mishra, S. M. Szczepanek, T. D. Nguyen, Nat Biomed Eng 2020, DOI: 10.1038/s41551-020-00650-4.
A. M. Rodgers, A. S. Cordeiro, R. F. Donnelly, Med Devices (Auckl) 2019, 12, 379.
E. Kim, G. Erdos, S. Huang, T. W. Kenniston, S. C. Balmert, C. D. Carey, V. S. Raj, M. W. Epperly, W. B. Klimstra, B. L. Haagmans, E. Korkmaz, L. D. Falo, Jr., A. Gambotto, EBioMedicine 2020, 55, 102743.
C. Kuwentrai, J. Yu, L. Rong, B. Z. Zhang, Y. F. Hu, H. R. Gong, Y. Dou, J. Deng, J. D. Huang, C. Xu, Bioengineering & Translational Medicine 2020, n/a, e10202.
X. Lan, W. Zhu, X. Huang, Y. Yu, H. Xiao, L. Jin, J. J. Pu, X. Xie, J. She, V. W. Y. Lui, H. J. Chen, Y. X. Su, Nanoscale 2020, 12, 18885.
Y. Ye, J. Wang, Q. Hu, G. M. Hochu, H. Xin, C. Wang, Z. Gu, ACS Nano 2016, 10, 8956.
C. Wang, Y. Ye, G. M. Hochu, H. Sadeghifar, Z. Gu, Nano Lett 2016, 16, 2334.
G. Chen, Z. Chen, D. Wen, Z. Wang, H. Li, Y. Zeng, G. Dotti, R. E. Wirz, Z. Gu, Proc Natl Acad Sci U S A 2020, 117, 3687.

* cited by examiner

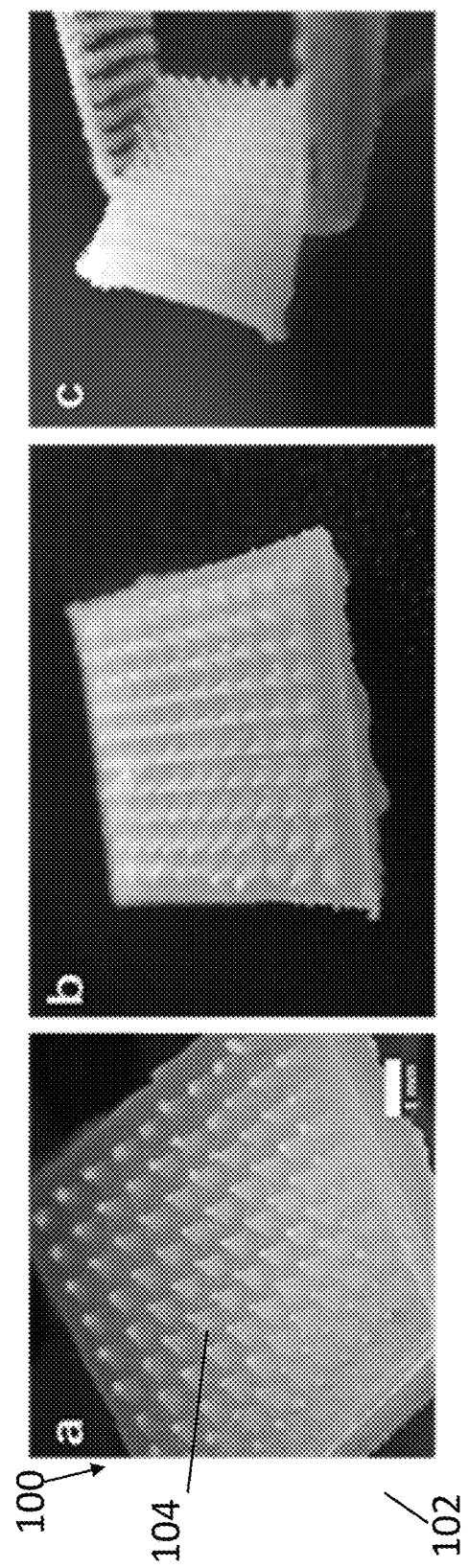
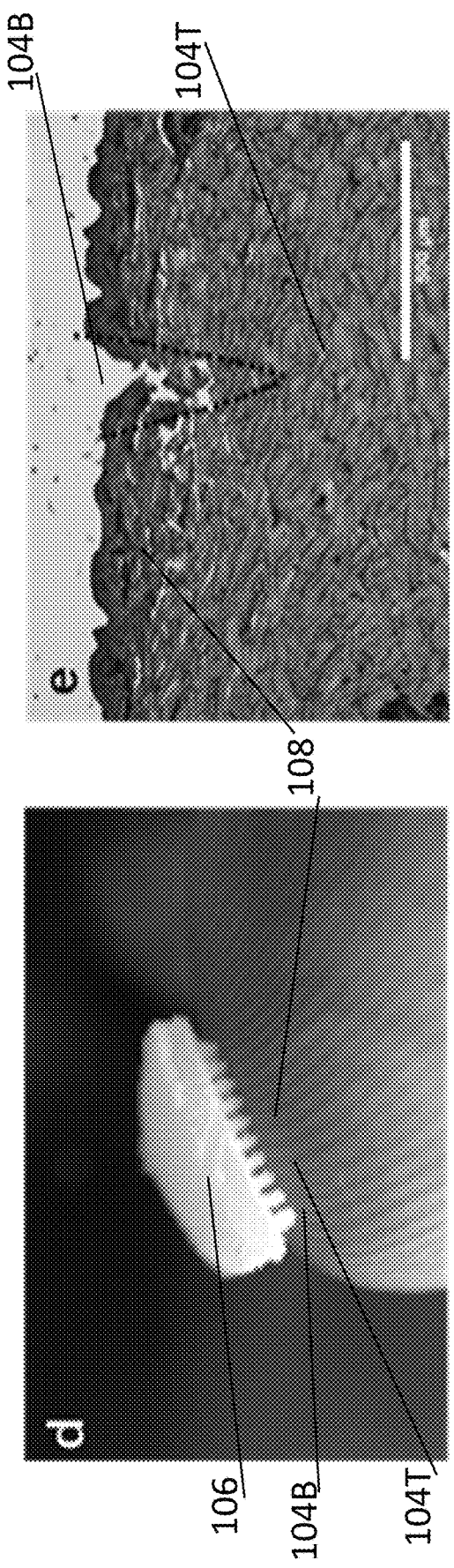

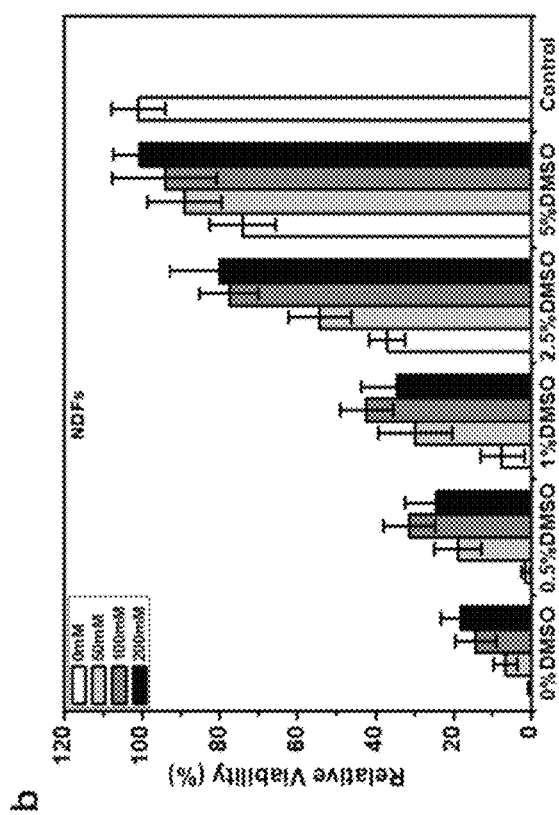
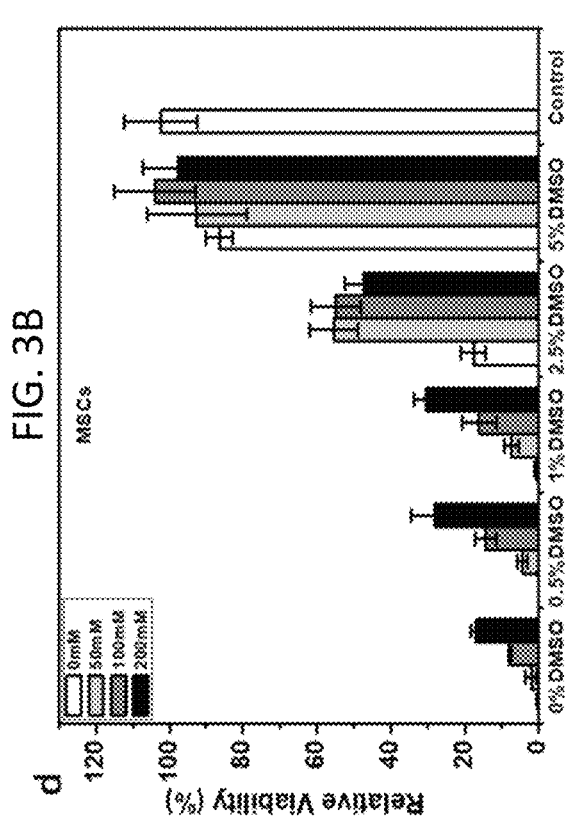
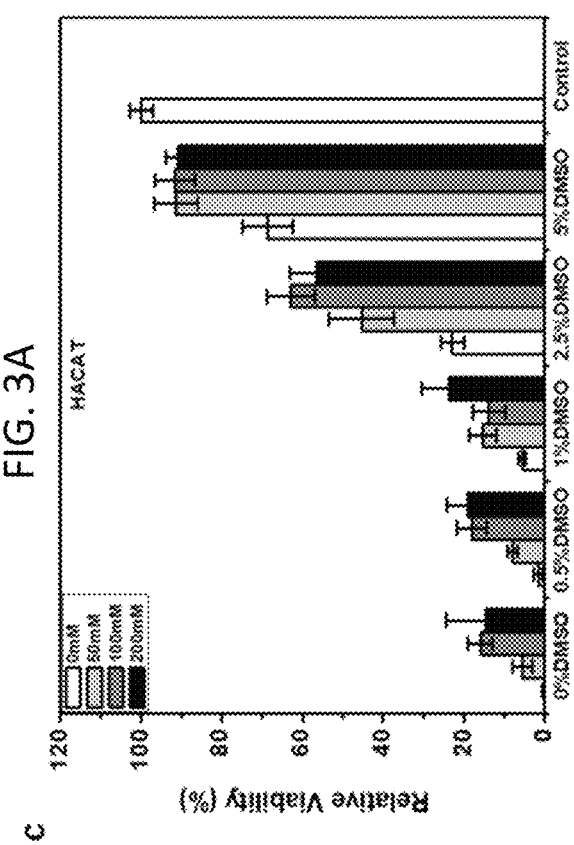
FIG. 3A
FIG. 3B
FIG. 3C
FIG. 3D

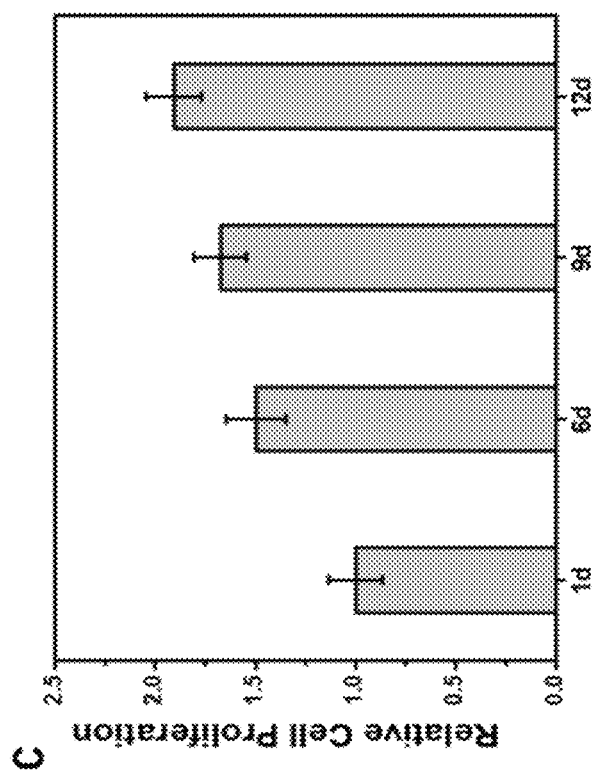
FIG. 6A
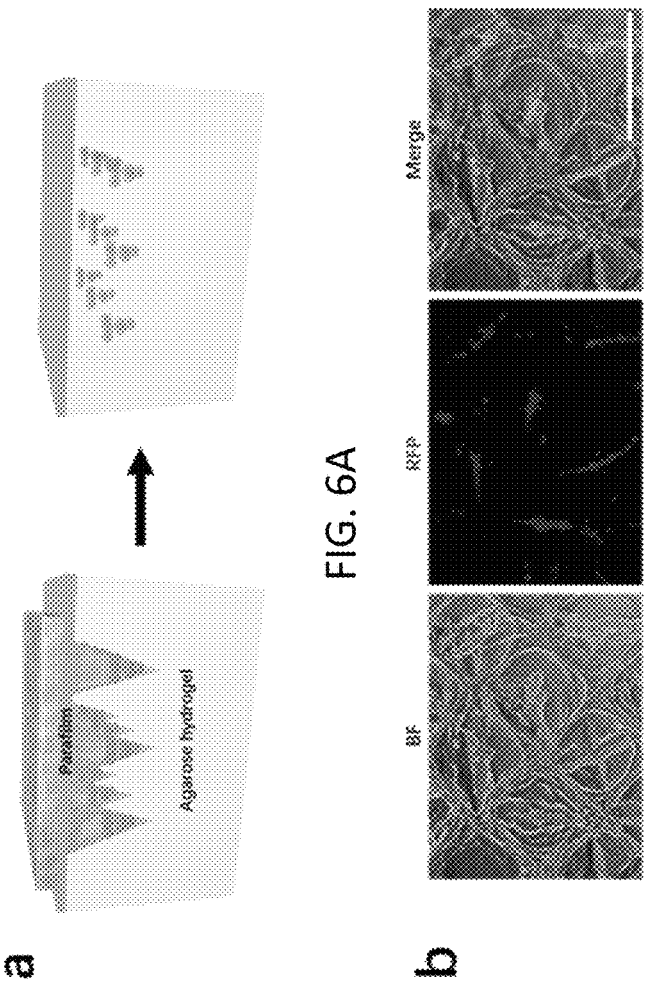
FIG. 6B
FIG. 6C

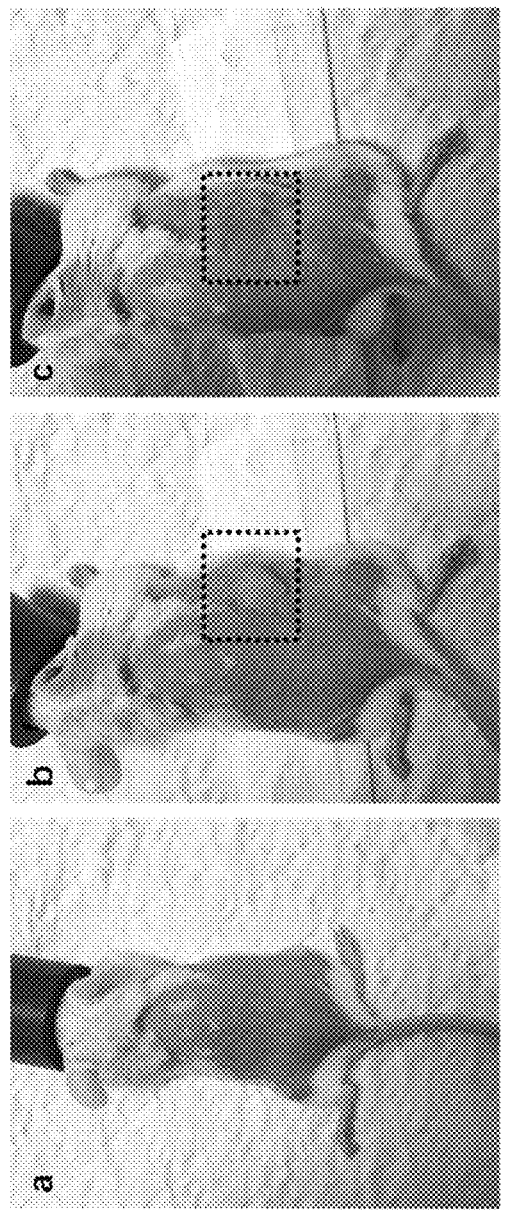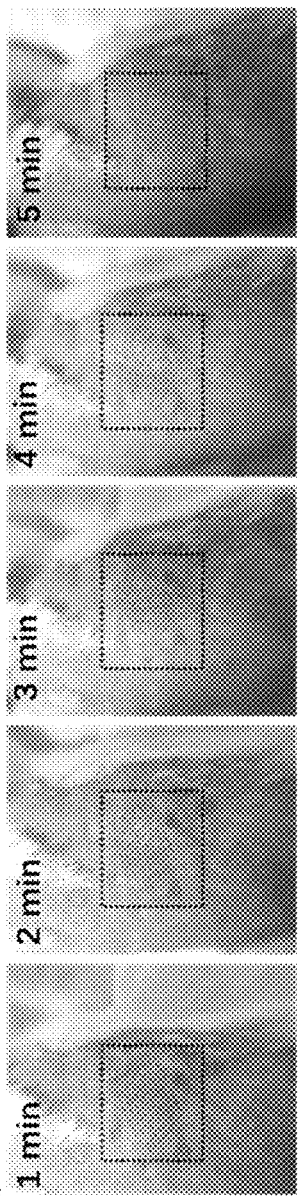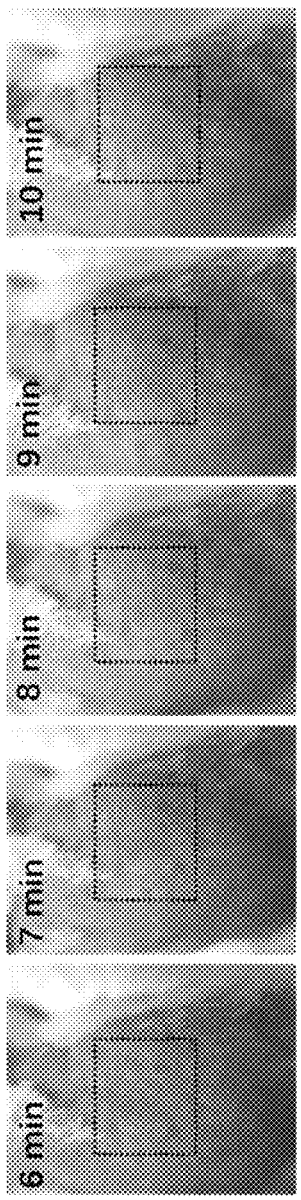
FIG. 8A  FIG. 8B  FIG. 8C  FIG. 8D

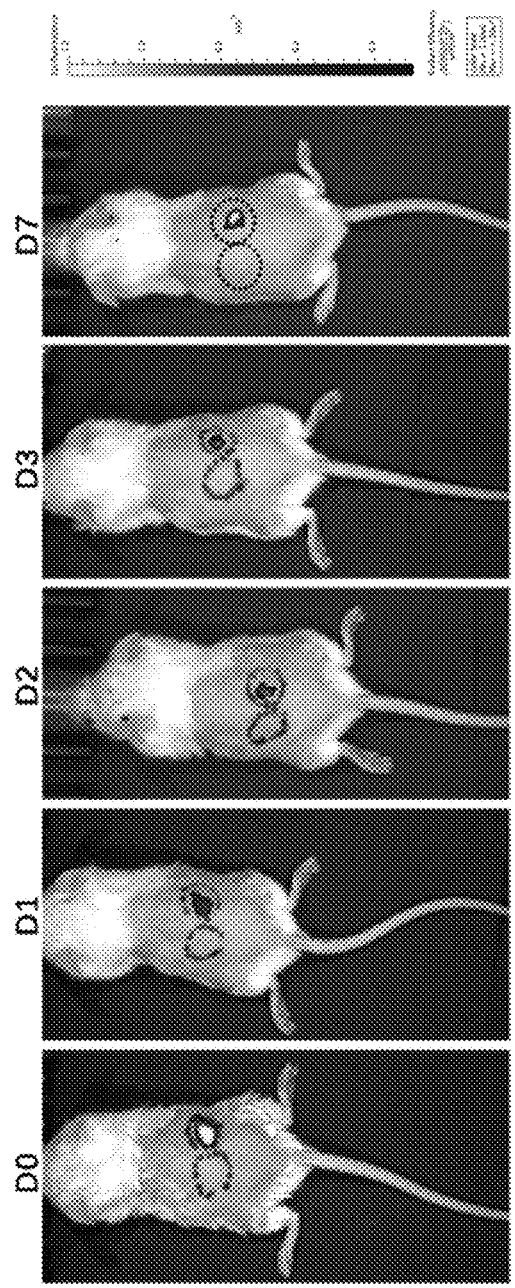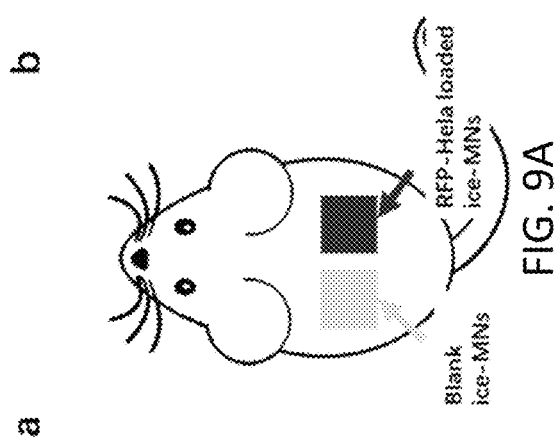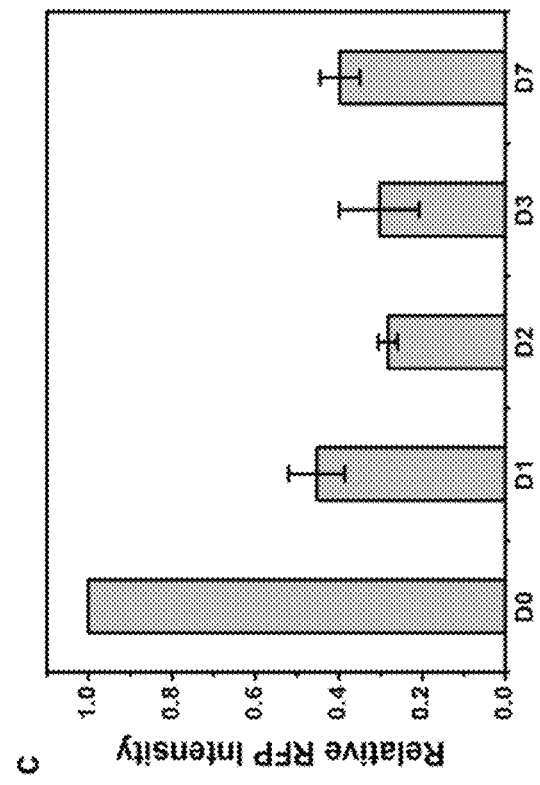
FIG. 9A
FIG. 9B
FIG. 9C

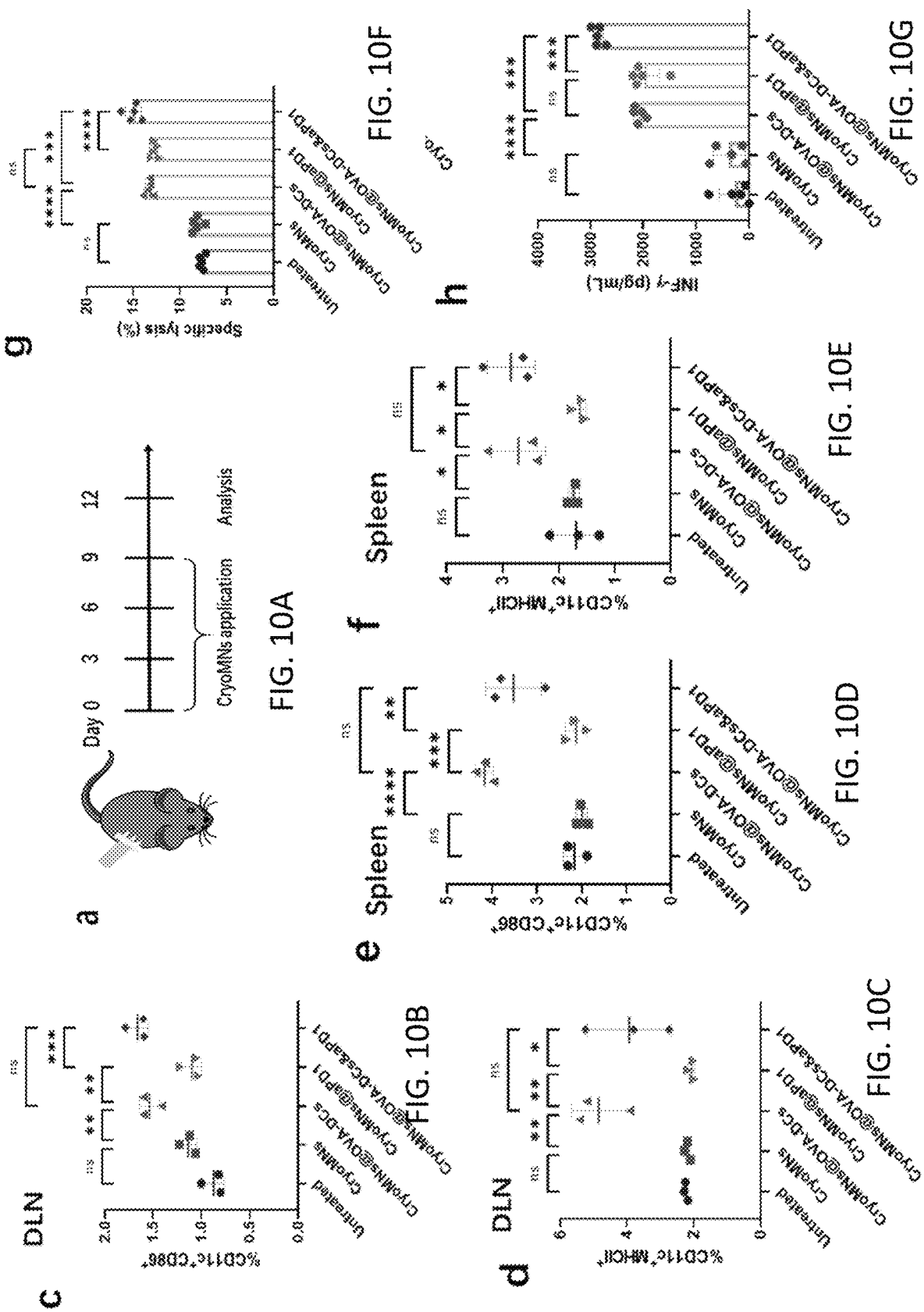

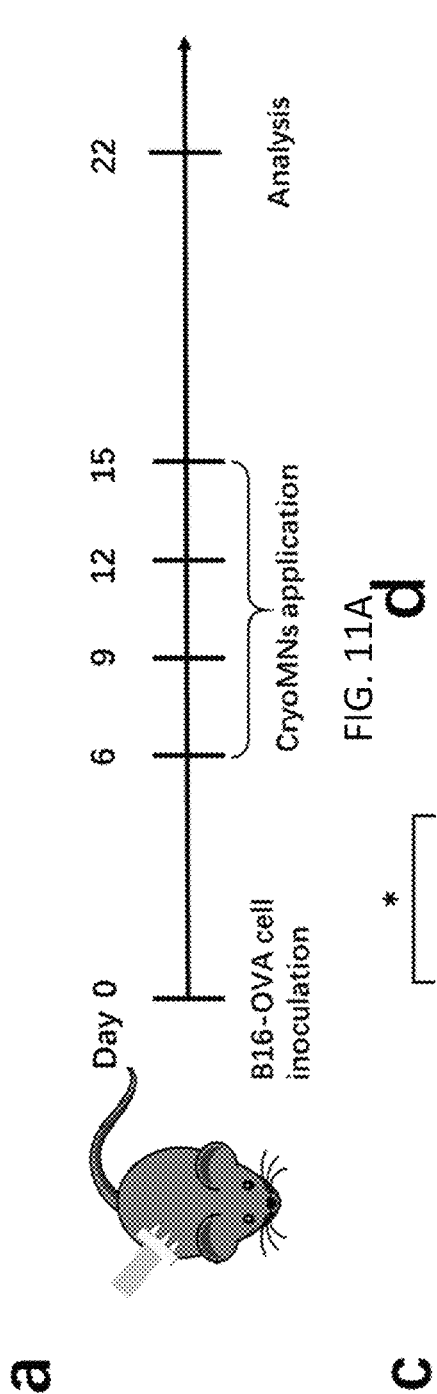
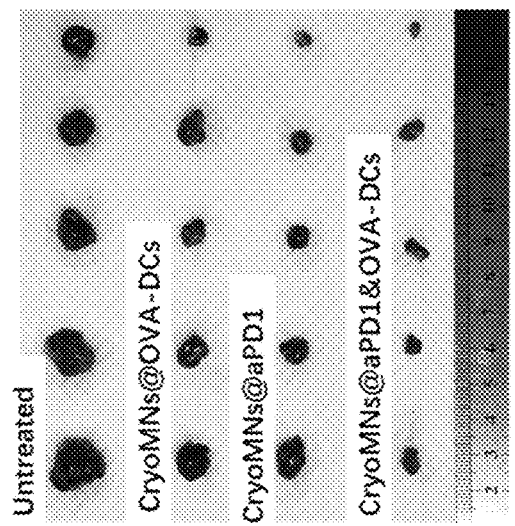
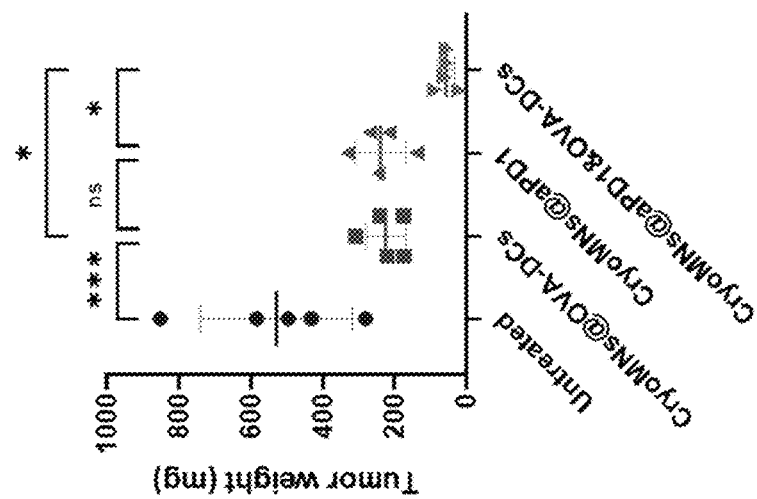
FIG. 11A
FIG. 11C
FIG. 11D

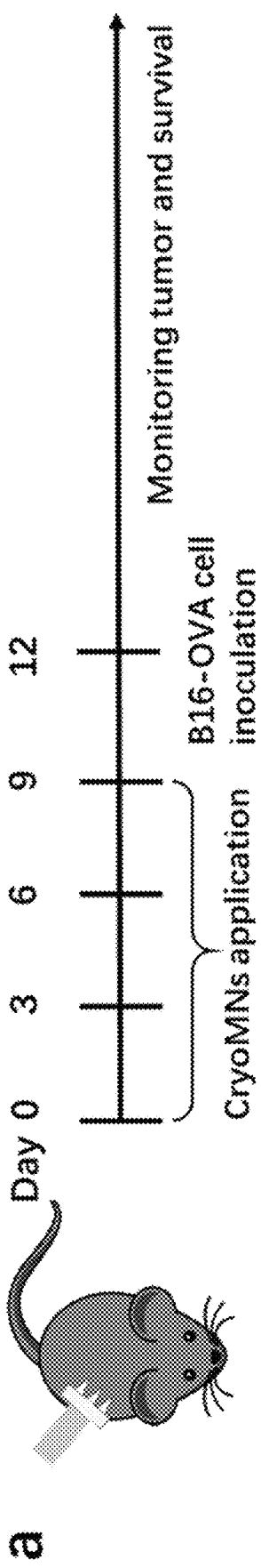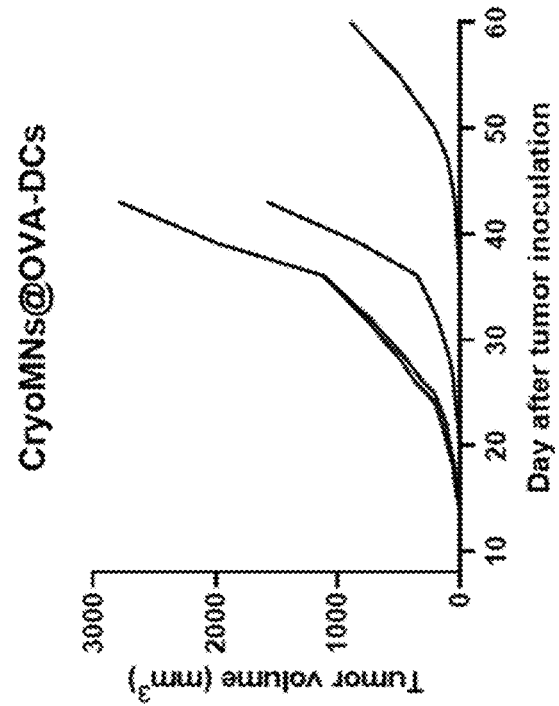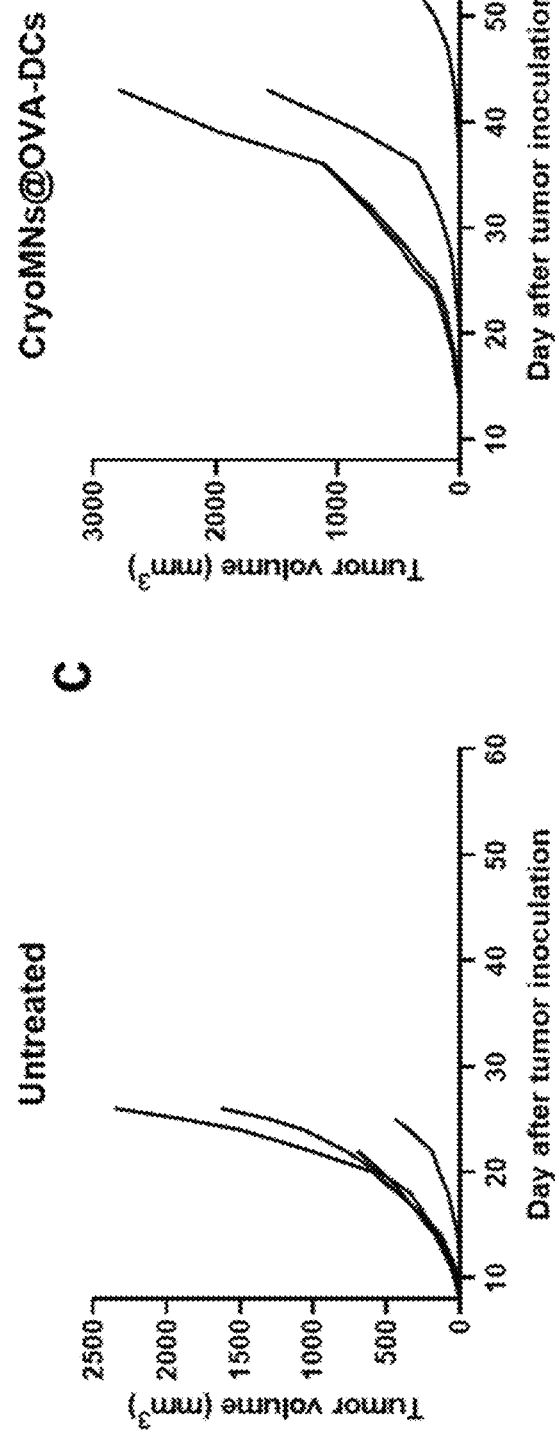
FIG. 13A
FIG. 13B
FIG. 13C

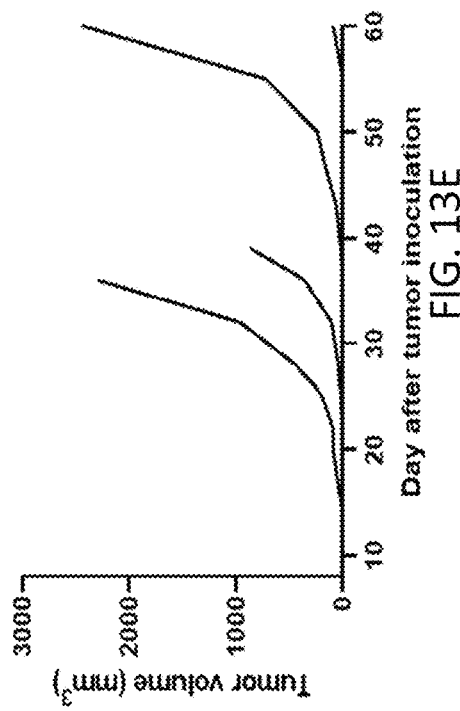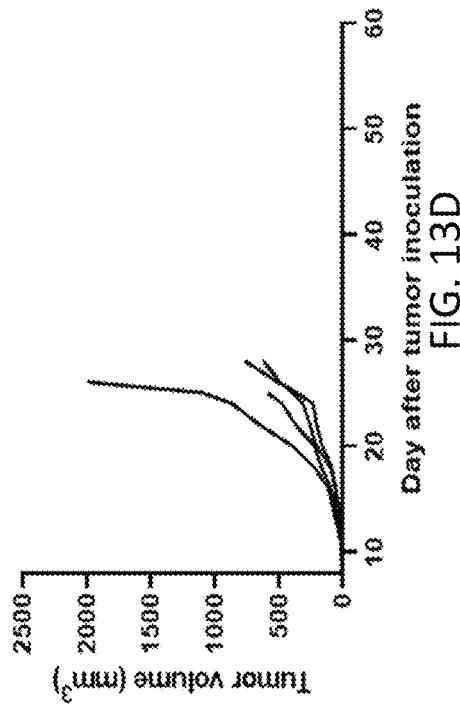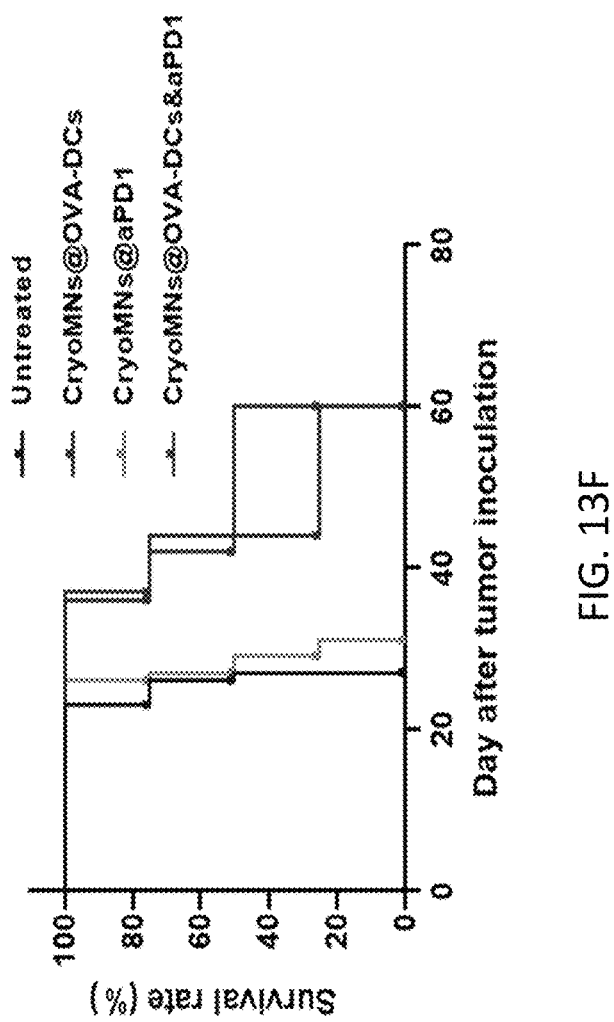
FIG. 13D
FIG. 13E
FIG. 13F

CRYO FORMULATION-BASED MICRONEEDLE DEVICE FOR TRANSDERMAL DELIVERY OF BIOACTIVE THERAPEUTIC AGENTS AND CANCER IMMUNOTHERAPY USING A CRYO-MICRONEEDLE PATCH

TECHNICAL FIELD

The present invention relates to a cryo formulation-based microneedle device for transdermal delivery of bioactive therapeutic agents, in particular, but not limited to transdermal delivery of bioactive therapeutic agents in cancer immunotherapy.

BACKGROUND

Delivery of bioactive agents is of great potential for treatment skin diseases. For example, melanocyte suspensions have been used clinically to vitiligo. Intradermal injection of fibroblast or mesenchymal stem cell was used for wound healing in recessive dystrophic epidermolysis bullosa.

In addition to treat skin diseases, transplantation of cells is also used in the field of facelift and hair regeneration. For example, injection of fibroblast can help restore the elasticity of skin and reduce winkles because fibroblasts can produce a large amount of collagen which can recover skin.

SUMMARY OF THE INVENTION

In accordance with a first aspect the present invention, there is provided a cryo formulation-based microneedle device for transdermal delivery of bioactive therapeutic agents, comprising: one or more microneedle patches each including an array of miniaturized needles, wherein each miniaturized needle defining a base end and a tip; and a substrate to which the base end of the array of miniaturized needles is attached or integrated thereto; wherein the microneedle patch is in a cryo status; wherein each of the one or more microneedle patch is adapted to be applied on a skin surface, in which the miniaturized needles penetrates into skin; and wherein the miniaturized needles is further arranged to melt so as to release one or more bioactive therapeutic agents into the skin to achieve a targeted therapeutic effect.

In an embodiment the first aspect, each of the one or more microneedle patches consisting of a matrix solution and the bioactive therapeutic agents.

In an embodiment the first aspect, the bioactive therapeutic agents comprise a plurality of biological cells including at least one of cancer cells, fibroblasts, endothelial cells, smooth muscle cells, stem cells, melanocytes, dendritic cells, neutrophils, and T-cells.

In an embodiment the first aspect, the bioactive therapeutic agents comprise a biochemical substance including at least one of drugs, vaccines, proteins, peptides, nucleic acids, bacteria, virus and fungi.

In an embodiment the first aspect, the bioactive therapeutic agents comprise antigen-presenting cells and at least one substance arranged to boost the therapeutic effect of the antigen-presenting cells.

In an embodiment the first aspect, the at least one substance includes an immune checkpoint inhibitor.

In an embodiment the first aspect, the immune checkpoint inhibitor includes antibodies against programmed cell death protein 1 (anti-PD-1), programmed death-ligand 1 (anti-PD-L1) or cytotoxic T-lymphocyte-associated protein (anti-CTLA-4).

In an embodiment the first aspect, the antigen-presenting cells include dendritic cells.

In an embodiment the first aspect, the antigen-presenting cells include antigen-pulsed dendritic cells.

In an embodiment the first aspect, the therapeutic effect includes activation of T-cells to enhance an antitumor immunity of the activated T-cells.

In an embodiment the first aspect, the matrix solution consists of an aqueous base solution and a cryoprotectant.

In an embodiment the first aspect, the aqueous base solution comprises at least one of water, saline, phosphate-buffered saline (PBS), and 4-(2-hydroxyethyl)-1-piperazineethanesulfonic acid (HEPES).

In an embodiment the first aspect, the cryoprotectant include at least one of dimethyl sulfoxide (DMSO), glycerol, ethylene glycol, sucrose, fructose, trehalose, galactose, dextrose and proteins.

In an embodiment the first aspect, the cryoprotectant include at least one of poly(ethylene glycol) (PEG), polyvinylpyrrolidone (PVP), polyvinyl alcohol (PVA), poly-l-lysine, hyaluronic acid (HA), starch, gelatin, agarose, alginate, chitosan, cellulose, carboxymethyl cellulose (CMC), collagen, chitin, dextran, guar gum, pullulan, xanthan, xyloglucan, heparin, chondroitin, keratan, mucin, and their derivatives thereof.

In accordance with a second aspect the present invention, there is provided a method of fabricating a microneedle device in the first aspect, comprising the steps of: casting the matrix solution containing the bioactive therapeutic agents into a mold defined with an array of microneedle structures; freezing the solution to define the array of microneedle structures on the microneedle patches; and dethatching the microneedle patches from the mold.

In an embodiment the second aspect, the mold includes a PDMS mold or a metal mold.

In an embodiment the second aspect, the method further comprises the step of urging the bioactive therapeutic agents and/or the matrix solution into the array of microneedle structures define on the mold.

In an embodiment the second aspect, the bioactive therapeutic agents and/or the matrix solution are driven into the mold using centrifugation.

In an embodiment the third aspect, there is provided a method of using the microneedle device of the first aspect, comprising the step of: removing the microneedle device from a storage place; and applying the microneedle device within a predetermined period of time after removal from the storage place.

In an embodiment the third aspect, the predetermined period of time is 1-30 seconds.

In an embodiment the third aspect, the microneedle patches are arranged to facilities a predetermined penetration depth of the bioactive therapeutic agents into the skin.

In an embodiment the third aspect, the predetermined penetration depth is 50-1000 μm.

In an embodiment the third aspect, the method further comprises the step of temporally attaching the microneedle device to a handle, thereby allowing an operator to apply the microneedle device by holding the handle.

The term "comprising" (and its grammatical variations) as used herein are used in the inclusive sense of "having" or "including" and not in the sense of "consisting only of".

It should be understood that alternative embodiments or configurations may comprise any or all combinations of two or more of the parts, elements or features illustrated, described or referred to in this specification.

Any reference to prior art contained herein is not to be taken as an admission that the information is common general knowledge, unless otherwise indicated. It is to be understood that, if any prior art information is referred to herein, such reference does not constitute an admission that the information forms a part of the common general knowledge in the art, in any other country.

As used herein, the term "and/or" includes any and all possible combinations or one or more of the associated listed items, as well as the lack of combinations when interpreted in the alternative ("or").

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting. Where specific integers are mentioned herein which have known equivalents in the art to which this invention relates, such known equivalents are deemed to be incorporated herein as if individually set forth.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Details and embodiments of the indoor navigation method and system will now be described, by way of example, with reference to the accompanying drawings in which:

FIGS. 1A to 1D are images showing different view of the ice microneedles integrated with living cells in accordance with embodiments of the present invention;

FIG. 1E is an image showing an H&E-stained cross-section of porcine skin after being penetrated by ice microneedles of FIG. 1A;

FIGS. 3A to 3F are plots showing relative viability of, RFP-Hela (a), NDFs (b), HACAT (c), MSCs (d), melanocytes (e) and T-cells (f), respectively, after being frozen in the solution with different concentrations of DMSO and sucrose at −80° C. for 1 day;

FIGS. 4A and 4B illustrate the viability of different types of cells after recovering from ice-MNs (freezer at −80° C.) patches and ice-MNs (LN) after 1 day storage, in which FIG. 4A shows live (green)/dead (red) staining of loaded cells, with the scale bar of 200 μm, and FIG. 4B is a plot showing quantitative data of viability obtained from the Live/Dead staining and Alarmablue™ viability assay;

FIGS. 6A to 6C illustrate a delivery of RFP-Hela cells into 3D hydrogel system, the RFP-Hela loaded ice-MNs were storage in LN for 1 day, and in which: FIG. 6A is a schematic illustration of ice-MNs(LN) penetrating into fake skin model made from 1.4% agarose gel and parafilm; FIG. 6B are microscopic images showing a top view of the hydrogel after application of ice-MN patches; and FIG. 6C is a plot showing the proliferation of RFP-Hela cells after being delivered into hydrogel;

FIGS. 8A to 8D are images showing an application of ice-MNs on mice, the RFP-Hela loaded ice-MNs were storage in LN for 1 day, in which FIGS. 7A to 7C respectively shows before (a), during (b) and after (c) application of ice-MNs (LN) on mice skin, wherein FIG. 7D shows a series of images showing the skin recovery post the treatment, and the microholes made by MN patch gradually disappeared within 10 min;

FIG. 9A is a Schematic diagram showing an application of RFP-Hela loaded ice-MNs (LN) in the mice model;

FIG. 9B are in vivo fluorescence images of RFP secreted by RFP-Hela after being delivered into skin;

FIG. 9C is a plot showing the quantitative data of RFP intensity in mice skin along with the time;

FIGS. 10A to 10G show in vivo immuno responses after vaccination with cryoMNs, in which FIG. 10A is a schematic showing the protocol of vaccination with OVA-DC-cryoMNs in mice; FIGS. 10B to 10E are plots showing quantification of the percentage of CD11c+CD86+DCs (c,e) and CD11c+MHCII+DCs (d,f) in draining lymph nodes (dLNs) and spleen excised from mice in different treatment groups analysed by flow cytometry; FIG. 10F is a plot showing determination of cytotoxic T lymphocyte (CTL) activity in vitro. Effector cells (splenocytes) and target cells (B16-OVA cells) were cocultured at different ratios, where "E:T" refers to the ratio of effector cells (E) and target cells (T); and FIG. 10G is a plot showing secretion level of IFN-γ in the culture supernatants after 48 h of culture;

FIG. 11A to 11G show a tumor treatment experiment in an example embodiment of the present invention, in which FIG. 11A is a schematic showing the protocol of the tumor treatment experiment; FIG. 11B is a plot showing tumor volume monitoring; FIG. 11C is a plot showing the tumor weight; FIG. 11D is an image showing the sizes of the tumor samples under different treatments; FIG. 11E is a plot showing mouse weight monitoring during experiment; and FIG. 11F to 11G are plots showing quantification of the percentage of CD3+CD8+ T-cells (g) and CD3+CD4+ T-cells (h) in tumor excised from mice in different treatment groups analysed by flow cytometry;

FIGS. 13A to 13F shows a tumor prevention experiment in an example embodiment of the present invention, in which FIG. 13A is a schematic showing the protocol of the tumor prevention experiment; FIGS. 13B to 13E are plots showing tumor volume monitoring under different treatment conditions; and FIG. 13F is a plot showing survival rate of the samples under different treatment conditions.

DETAILED DESCRIPTION OF THE PREFERRED EMBODIMENT

Figure 2:
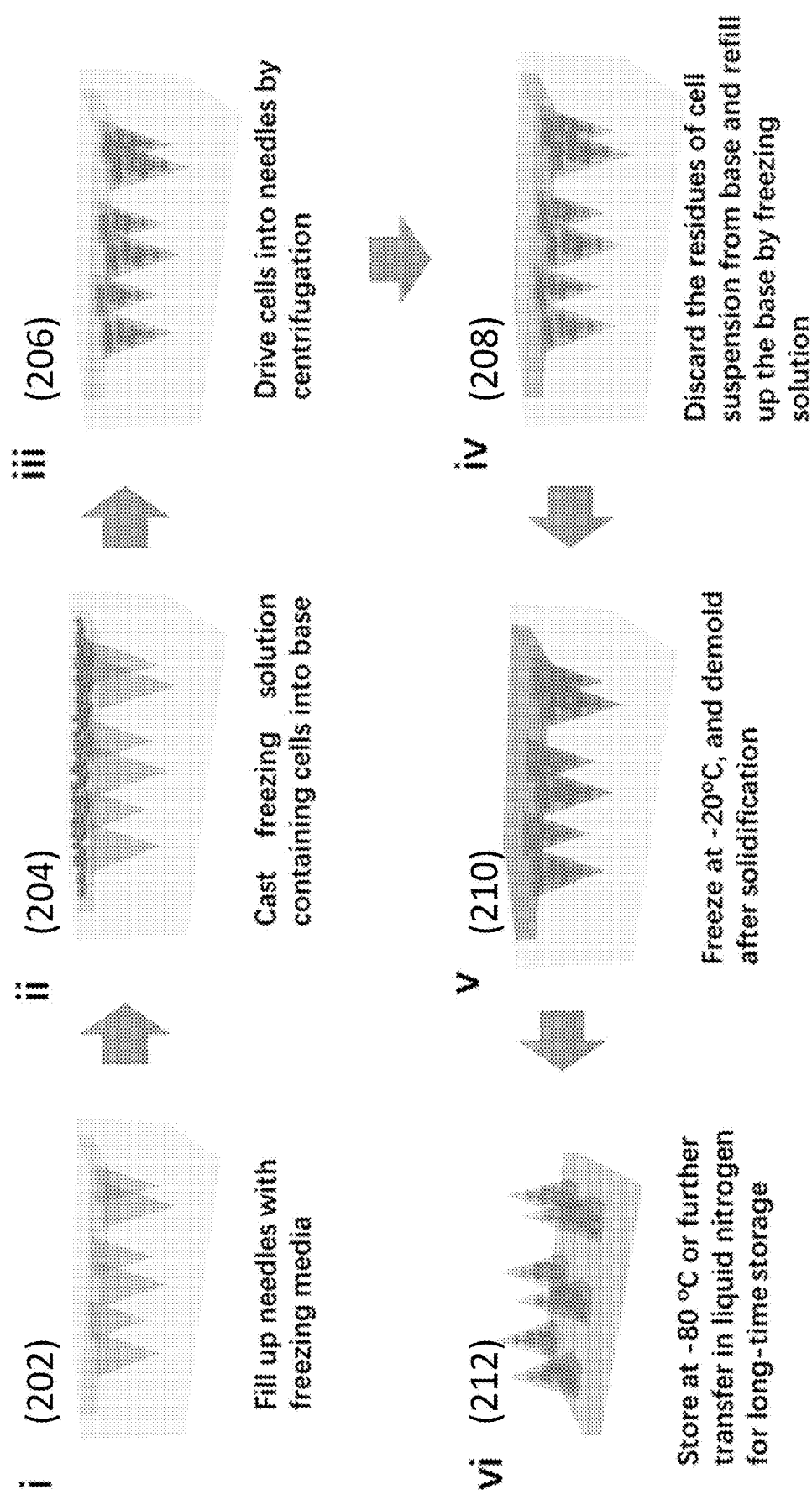
FIG. 2 is an illustration showing a process flow of a fabrication of ice microneedles integrated with living cells in accordance with an embodiment of the present invention.
Figure 3F:
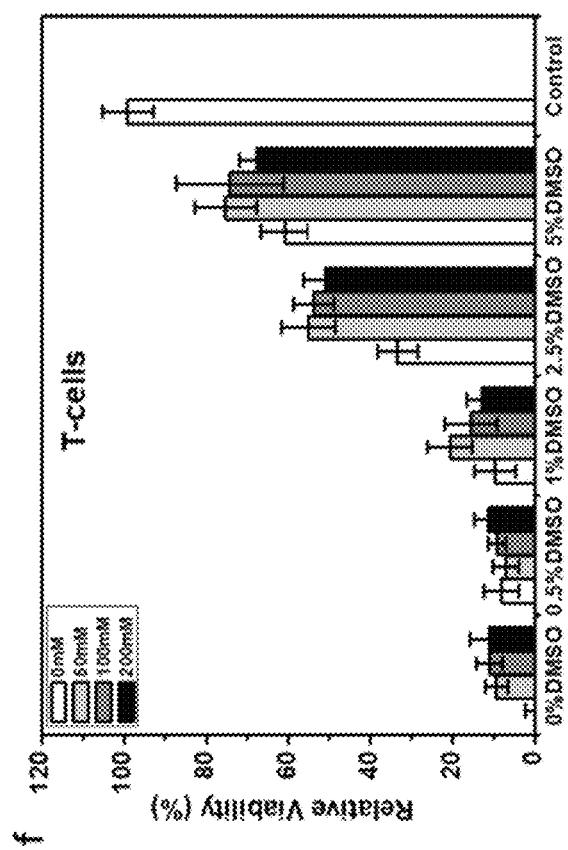
Figure 3E:
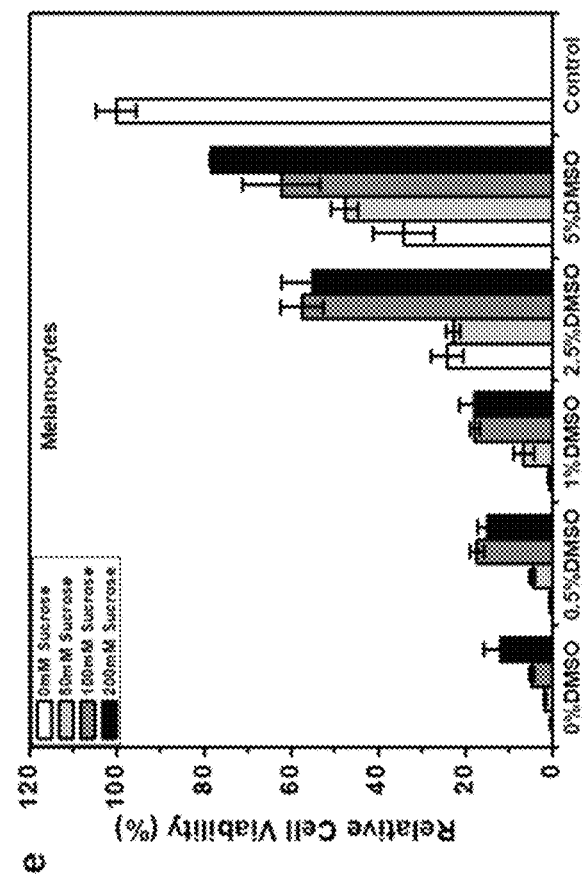

The inventors, through their own research, trials and experiments, devised that microneedles (MNs) are an array of miniaturized needles down to the micrometer scale and they are initially developed for transdermal delivery of drugs and vaccines. They allow for the minimally-invasive perturbation of the stratum corneum barrier and controlled and targeted delivery of therapeutic agents in pain-free and blood-free fashion. Recently, they are also used for the extraction of blood and interstitial fluid for biomarker analysis. MN-based devices have low risk of infection, needle-phobic and needle-stick injury and cross-contamination.

In some example embodiments, MNs may be made of silicon, metals (e.g. stainless-steel and titanium), ceramics, and polymers. However, silicon, metal and ceramics based MNs suffer from the limited drug loading, potential break-up in skin, or complicated and expensive fabrication procedures, and polymer MNs are limited by the low drug loading and inability to maintain the activity and deliver fragile active agents such as protein, plasmid, stem cells, immune cells, bacteria, and virus.

In accordance with an embodiment of the present invention, there is provided a new class of MN device, the cryo formulation-based MN device (cryo MNs, or ice MNs), which is significantly different from the abovementioned MN platforms in terms of materials, formulations, and fabrication protocols.

Preferably, this device is made of aqueous solutions and bioactive therapeutic agents (eg. cells, drugs, and proteins, et al.) and fabricated by freezing to form the cryo status. The formulation is optimized to maximize the bioactivity of therapeutic agents while providing sufficient mechanical properties for the ice MNs to penetrate into the skin layers. Finally, the ice MNs are usually made right before usage within the template (can be less than 4 hours), but can be stored for at least 1 month without loss of bioactivity or viability.

In one example embodiment, the invention provides a direct integration of cells and delivery of cells with ice MNs. The inventors devise that all other MN platforms except hollow MNs are not suitable for cell delivery, and although hollow MNs may be used to deliver cells through pressure-based injection, such system lacks of control of the injection depth, cell number, and pattern of cells.

Preferably, the ice MNs is the first type of solid MN that can deliver cells and directly integrate cells into MNs. It offers a convenient strategy to control the location, density and types of delivered cells in skin.

With reference to FIGS. 1A to 1E, there is shown an example embodiment of a cryo formulation-based microneedle device 100 for transdermal delivery of bioactive therapeutic agents, comprising: one or more microneedle patches 102 each including an array of miniaturized needles 104, wherein each miniaturized needle 104 defining a base end and a tip 104T; and a substrate 106 to which the base end of the array of miniaturized needles 104 is attached or integrated thereto; wherein the microneedle patch 102 is in a cryo status; wherein each of the one or more microneedle patch 102 is adapted to be applied on a skin surface 108, in which the miniaturized needles 104 penetrates into skin; and wherein the miniaturized needles 104 is further arranged to melt so as to release one or more bioactive therapeutic agents into the skin to achieve a targeted therapeutic effect.

In this example, the microneedle patches 102 consisting of a matrix solution containing a bioactive therapeutic agents being freezed in the solid state, such that when the ice microneedle patches 102 is subjected to heat at the skin surface 108 and/or from the environment, it melts gradually and hence the bioactive therapeutic agents is released into the skin as the patch 102 melts.

Examples of bioactive therapeutic agents may includes biological cells, such as but not limited to cancer cells, fibroblasts, endothelial cells, smooth muscle cells, stem cells, melanocytes, dendritic cells, neutrophils, and T-cells. Alternatively or additionally, the bioactive therapeutic agents may include other biochemical substances such as but not limited to drugs, vaccines, proteins, peptides, nucleic acids, bacteria, virus and fungi.

The bioactive therapeutic agents may be contained in a matrix solution, comprising an aqueous base solution and a cryoprotectant, such that the matrix solution and the bioactive therapeutic agents may be molded to have the shape of the microneedles 104 with the base. Examples of the aqueous base solution includes one or more of saline, water, phosphate-buffered saline (PBS), and 4-(2-hydroxyethyl)-1-piperazineethanesulfonic acid (HEPES), and these aqueous base solution may be solidified upon freezing.

For example, the ice-MNs that were finally frozen either in −80° C. or liquid nitrogen (LN) were named as ice-MNs (−80° C.) and ice-MNs (LN), respectively. The morphology of ice MNs 104 is shown in the FIGS. 1A to 1D. In this example, the obtained ice-MNs 104 displayed a height of ~900 μm with a base width of about 350 μm and inter-needle spacing of about 350 μm. According to the dimension of ice-MN patch 102 and volume formula of rectangular pyramid, the volume of solution in each needle cavity was about $3.7 \times 10^{-2}$ μL. In addition, referring to FIG. 1E, the ice MNs can easily penetrate cross the epidermis and reach to dermis. It should be appreciated by a skilled person in the art that the dimension or design parameters of the MNs including the size, pitch, height and shape of the needles, as well as the area of the MNs array may be changed according to different application which requires delivery of bioactive therapeutic agents through the skin surface.

The formulation of solution for preparing ice MN depends on the desired active agents that will be delivered. The following table lists a number of example choice of several freezing solutions for different active agents.

| Active agents | Solutions |
| --- | --- |
| Cells | Water + cryoprotectants (such as 2.5% wt DMSO, 100 mM sucrose) |
| Protein/peptides | Water/PBS + 1 mg/mL Bovine serum albumin (BSA) |
| DNA/RNA | Water/PBS + 1 mg/mL polycation (such as poly-l-lysine, chitosan, collagen, polyethylenimine (PEI) and/or protamine) |
| Small molecular drugs | Water/PBS |

With reference to FIG. 2, there is shown an example fabrication process 200 for fabricating the microneedle device 100 in accordance with embodiments of the present invention. The method 200 of fabrication comprises the steps of: casting the matrix solution containing the bioactive therapeutic agents into a mold, such as a PDMS mold, defined with an array of microneedle structures; freezing the solution to define the array of microneedle structures on the microneedle patches; and dethatching the microneedle patches from the mold. Alternatively, a metal mold, such as a stainless steel mold, may be used.

Optionally, the method further comprises the step of urging the bioactive therapeutic agents and/or the matrix solution into the array of microneedle structures define on the mold, such as by using centrifugation.

Take 2.5% wt DMSO combined with 100 mN sucrose as an example, to fabricate ice MNs 104 for cell delivery, at step 202, the mold defining the shape of the needles may be filled up with the freezing media, such as the matrix solution or the mixture of 2.5% wt DMSO combined with 100 mM sucrose. At step 204, cells contained in a freezing solution such as water and/or the cryoprotectants are casted to the mold at the base. At step 206, the cells are driven into the needle structures using centrifugation. At step 208, the residues of cell suspension from the base may be discarded, and then the base of the mold may be refilled to form the base of the MN device.

At step 210, the matrix solution and the cells are frozen below the melting point of the matrix solution, e.g. at −20° C., followed by demolding the frozen patch after solidification. Finally, at step 212, the fabricated cryo formulation-based microneedle device may be stored under −80° C. and/or any other suitable environment, such as in liquid nitrogen, for long-time storage if necessary.

In an alternative example, to fabricate ice MNs for small molecular drug delivery, small molecular drug may be dissolved in aqueous with desired concentrations. The prepared solution is casted into PDMS mold and followed by centrifugation. Then the PDMS mold is put at −20° C. for 2 hours and then transferred to −80° C. Then Ice MN integrated with small molecular drugs can be peeled out of PDMS mold before applications.

Alternatively, to fabricate ice MNs for proteins/peptides delivery, proteins/peptides and BSA (1 mg/mL) may be dissolved in aqueous solution with desired concentrations. The prepared solution is casted into PDMS mold and followed by centrifugation. Then the PDMS mold is put at −20° C. for 2 hours and then transferred to −80 BC. Then Ice MNs integrated with small molecular drugs can be peeled out of PDMS mold before applications.

Yet alternatively, to fabricate ice MNs for DNA/RNA delivery, the DNA/RNA and polycations (1 mg/mL) are dissolved in aqueous solution with desired concentrations. The prepared solution is casted into PDMS mold and followed by centrifugation. Then the PDMS mold is put at −20° C. for 2 hours and then transferred to −80° C. Then Ice MN integrated with small molecular drugs can be peeled out of PDMS mold before applications.

The solutions for making ice MNs consist of aqueous base solutions and cryoprotectants. The aqueous base solutions may include saline, water, PBS, and/or HEPES. The cryoprotectants include DMSO, glycerol, ethylene glycol, sucrose, fructose, trehalose, galactose, dextrose, proteins, or any types of combination of two or more cryoprotectants. The cryoprotectants also include polyvinylpyrrolidone, polyvinyl alcohol, poly-l-lysine, HA, starch, gelatin, agarose, alginate, chitosan, cellulose, collagen, chitin, dextran, guar gum, pullulan, xanthan, xyloglucan, and their derivatives, and the combinations thereof. In addition, the cryoprotectants include the hydrogel systems made from abovementioned polymers.

To optimize the freezing solution for cell delivery, in an experiment performed by the inventors, six types of cells, including Hela-red fluorescent protein (RFP) stable human cell line (RFP-Hela), human keratinocytes (HACAT), human normal dermal fibroblasts (NDFs), human mesenchymal stem cells (MSCs), human melanocytes and human immune cells (T-cells) were frozen in the solution with different concentration of DMSO and sucrose. The results were shown in FIGS. 3A to 3F. Increasing DMSO concentration brings the decrease of mechanical property of ice MNs. In one preferable embodiment, to balance the mechanical property and cell viability, the optimal formulation of freezing solution for cell delivery is the combination of 2.5 wt % DMSO with 100 mM sucrose.

Figures 4A, 4B:
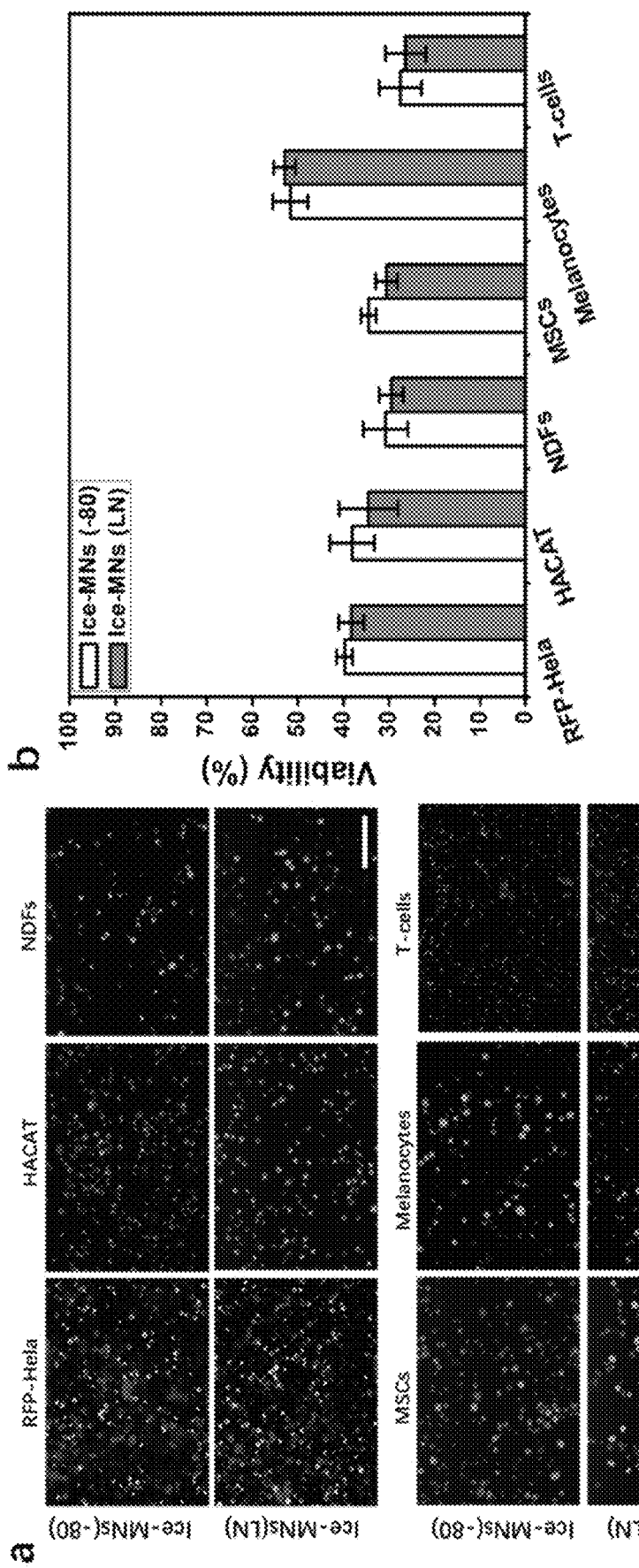
Figure 5A:
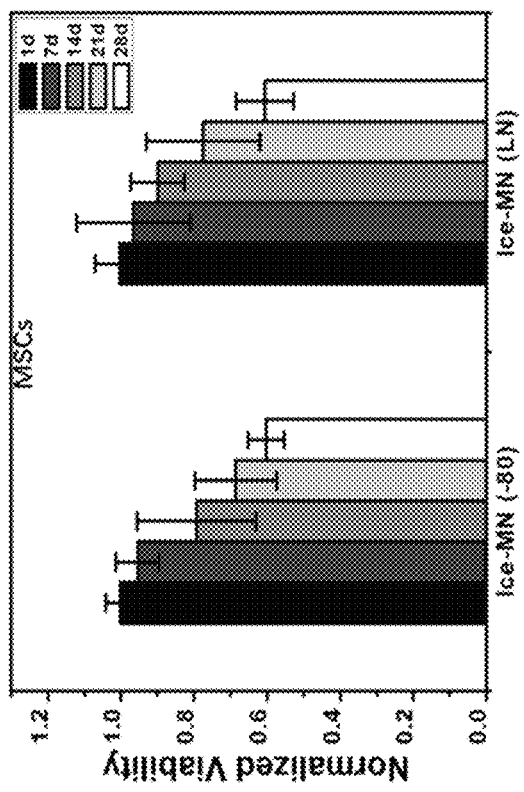
FIG. 5A to 5C are plots showing the viability of RFP-Hela (a), MSCs (b) and melanocytes (c), respectively, after recovering from ice-MNs (−80° C.) and ice-MNs (LN) for long-time storage.
Figure 5B:
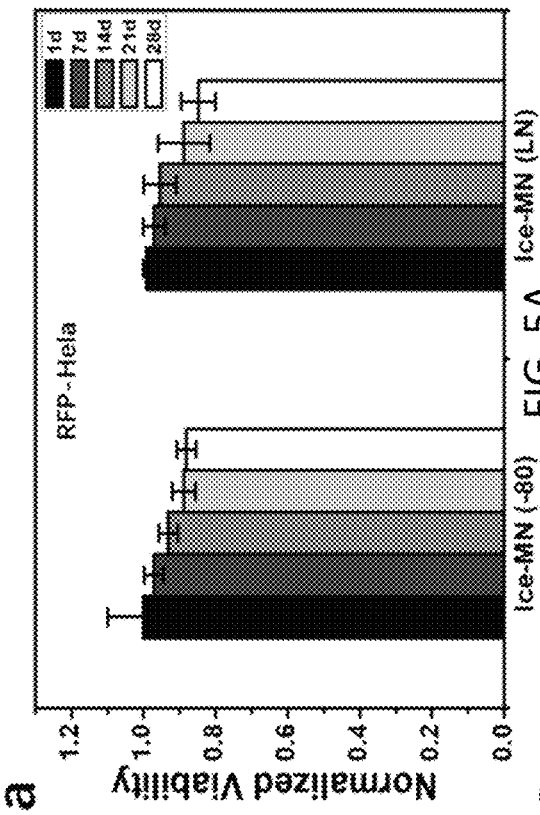
Figure 5C:
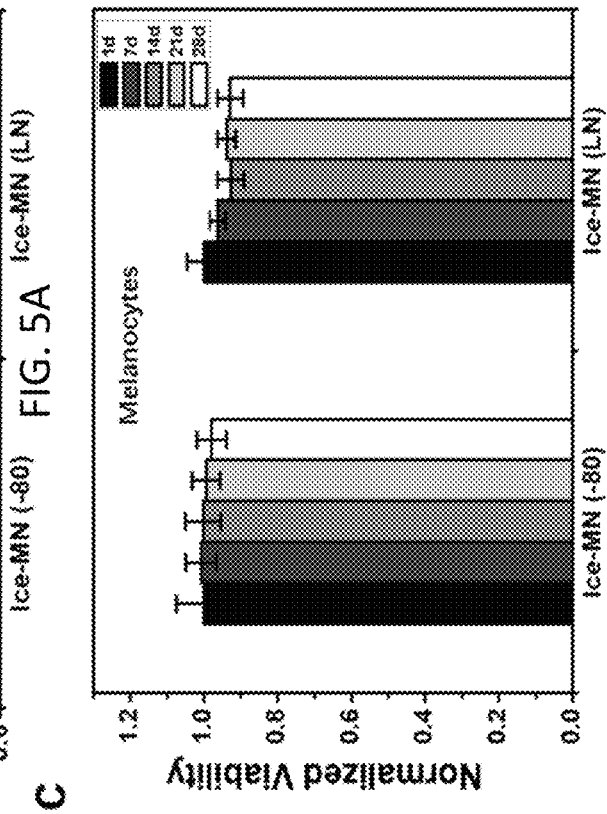

Furthermore, with reference to FIGS. 4A and 4B, the six types of cells were integrated in ice MNs and stored at freezer (−80° C.) and LN for 1 day. All types of cells maintained about 30% viability after 1-day storage. In addition, the viability of RFP-Hela, MSCs and melanocytes that were loaded in ice-MNs (−80° C.) and ice-MNs (LN) for long time storage were also tested. Referring to FIGS. 5A to 5C, it shows that cells could still maintained alive after being stored for 28 days.

Figure 6D:
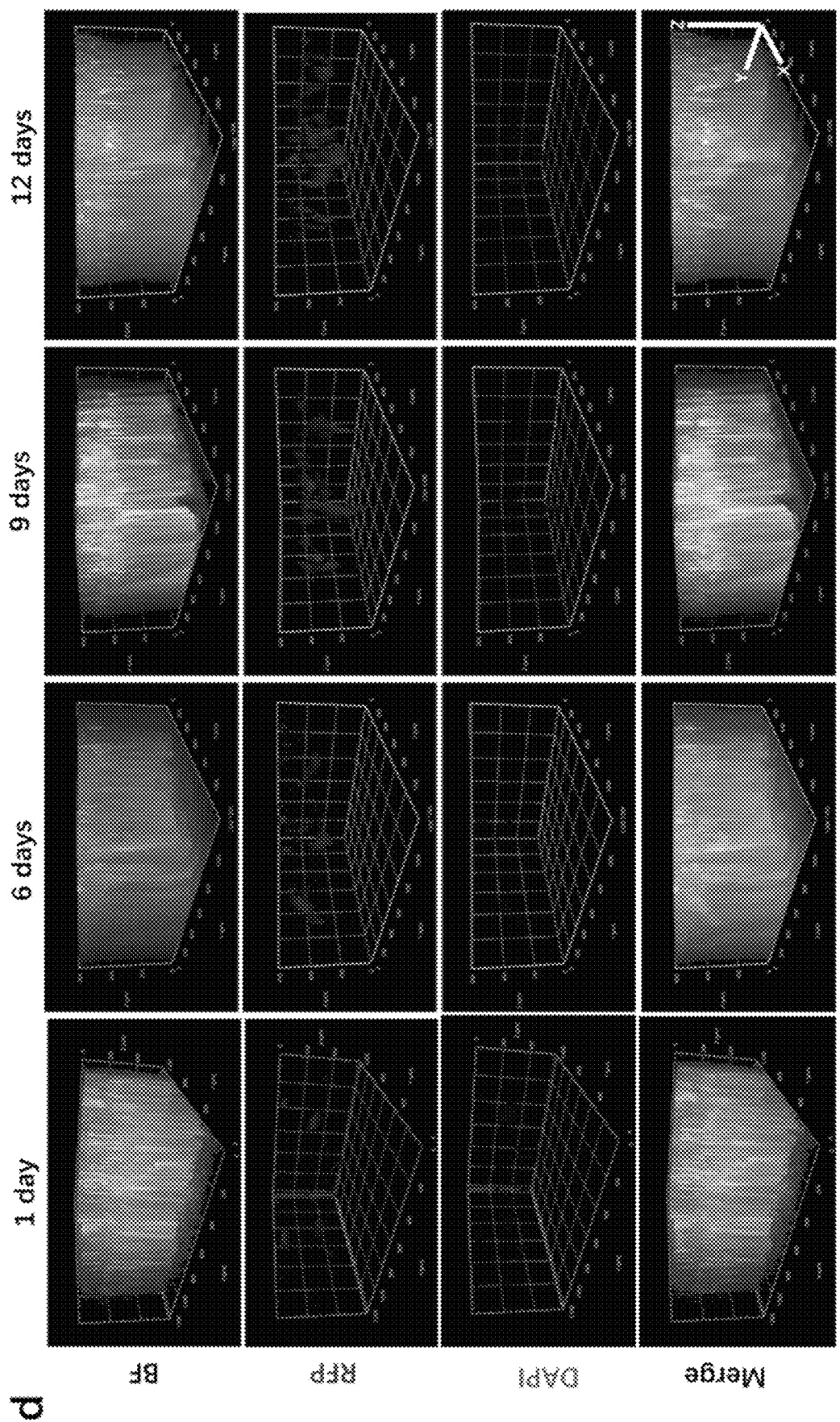

For the following experiment, the RFP-Hela loaded ice-MNs (LN) were selected as studying group and directly used after 1-day storage. The ice-MNs can successfully deliver the RFP-Hela into 3D hydrogel system (fake skin model) and the alive RFP-Hela could proliferate in this system, as shown in FIG. 6.

Figure 7B:
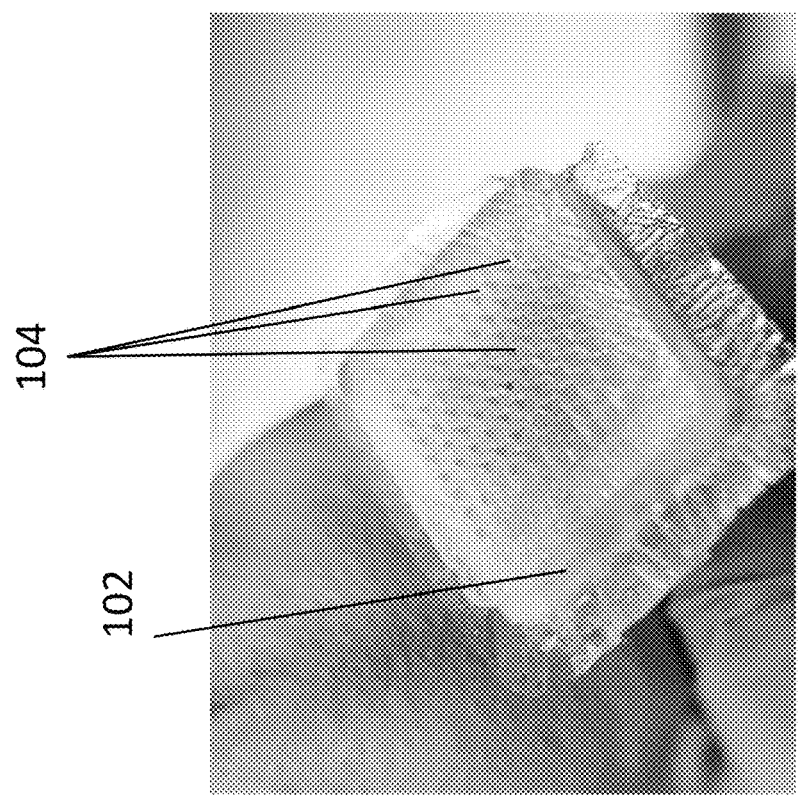
FIGS. 7A and 7B are images showing a cryo formulation-based microneedle device in accordance with an embodiment of the present invention, in which the microneedle device is attached to a handle.
Figure 7A:
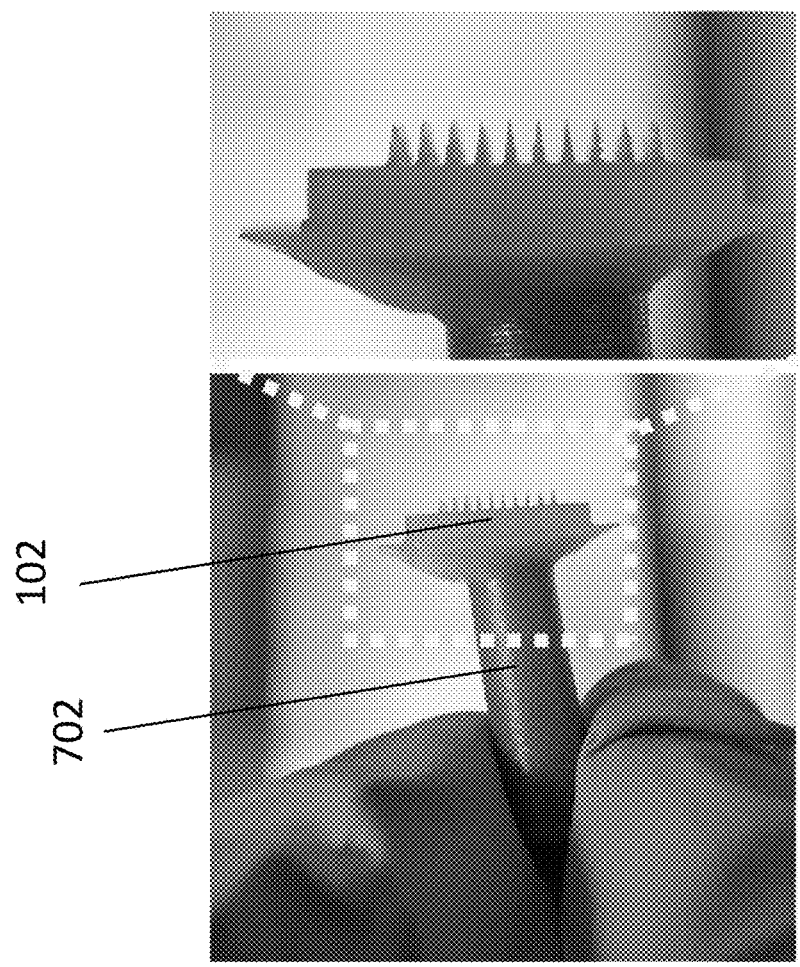
Figure 11B:
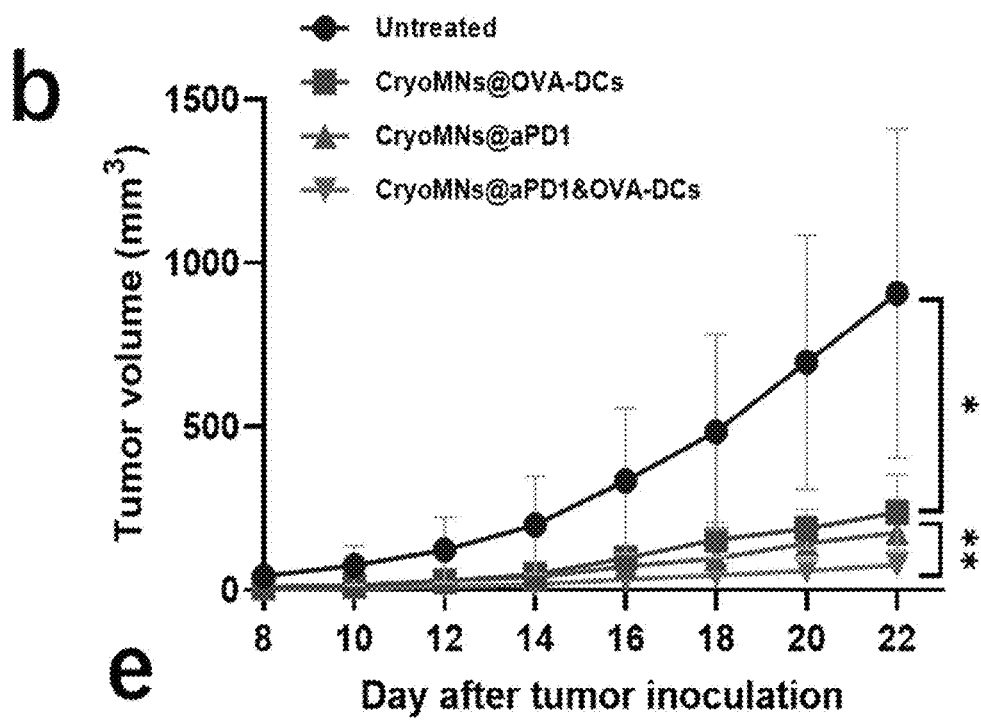
Figure 11E:
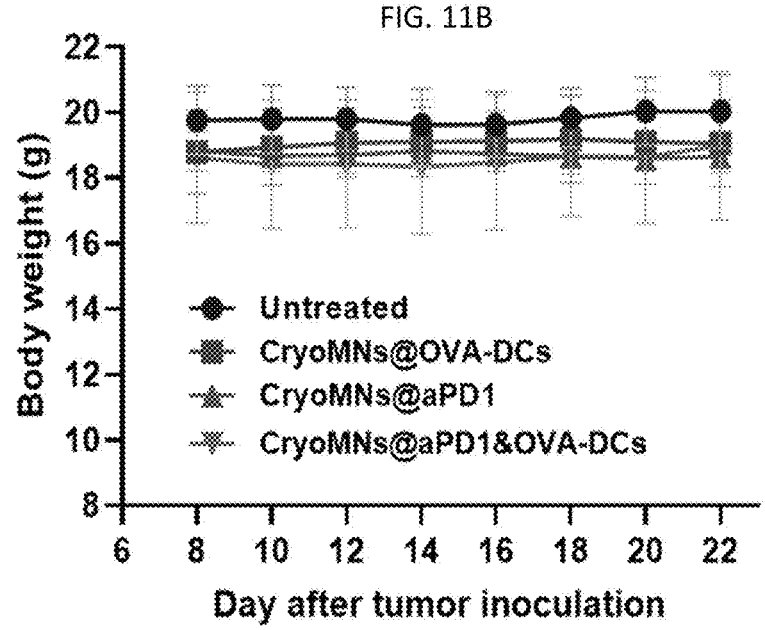
Figure 11G:
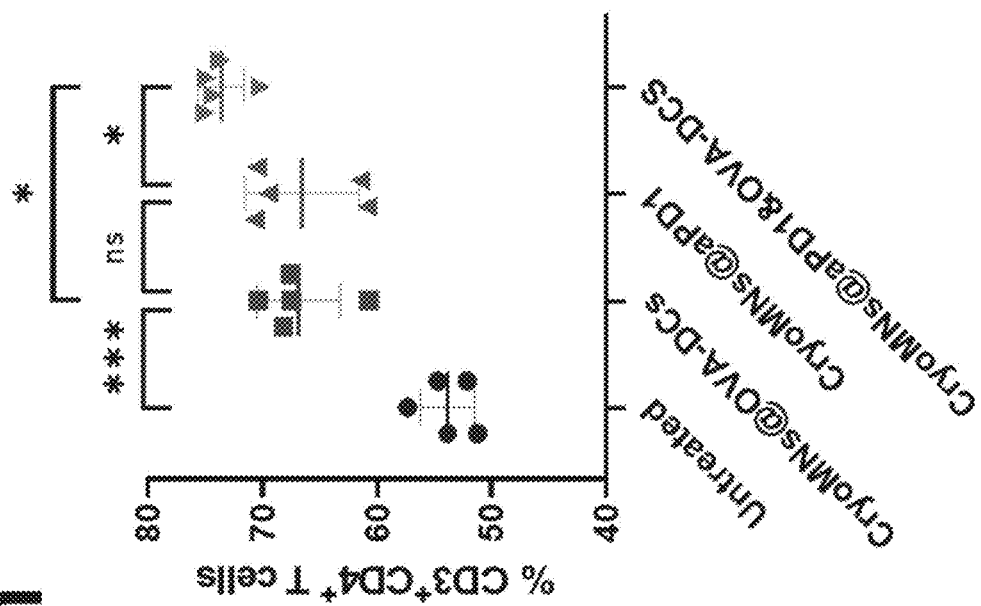
Figure 11F:
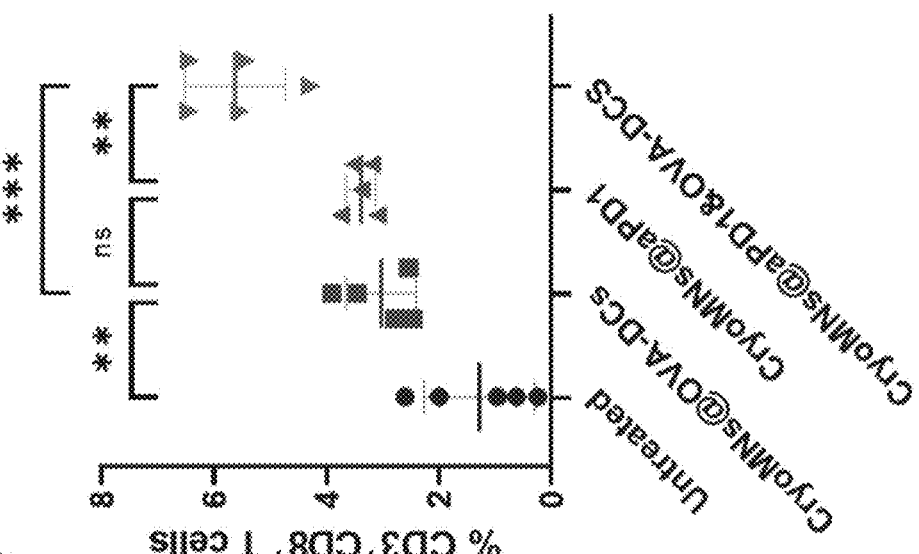
Figure 12:
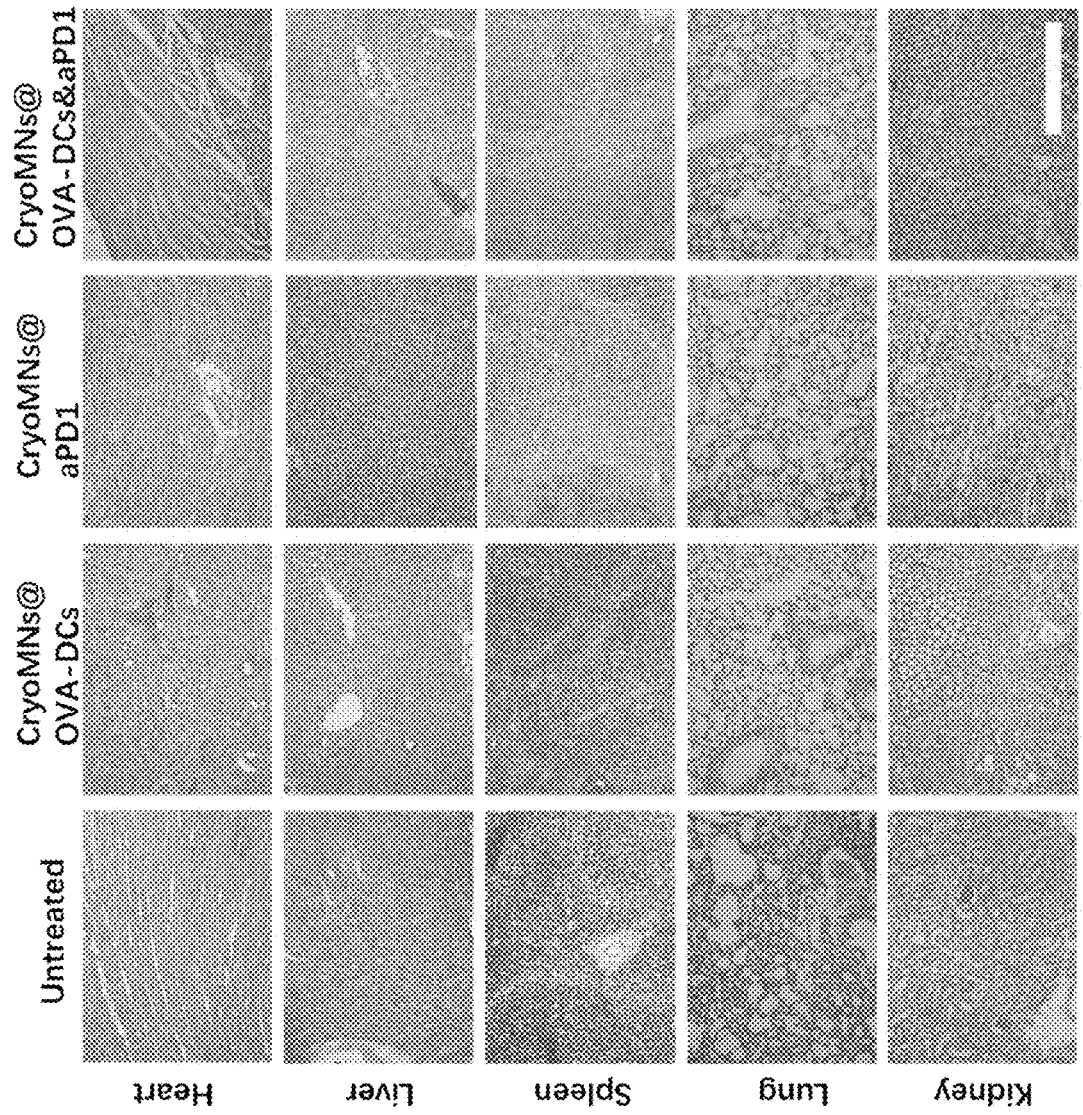
FIG. 12 are stain images showing H/E staining of major tissues in tumor treatment model.

With reference to FIGS. 7A and 7B, there is shown an embodiment of using the microneedle device 100 as described earlier, for example to deliver a certain dosage of RFP-Hela to mice using the MN patches 102. The method comprises the step of: removing the microneedle device 100 from a storage place; and applying the microneedle device 100 within a predetermined period of time, such as 30 seconds, after removal from the storage place.

Preferably, the microneedle patches 102 are arranged to facilities a predetermined penetration depth, such as 50-1000 μm, of the bioactive therapeutic agents into the skin.

Optionally, the method further comprises the step of temporally attaching the microneedle device 100 to a handle 702, thereby allowing an operator to apply the microneedle device 100 by holding the handle 702. For example, referring to FIGS. 7A and 7B, a rod shape handle 702 may be attached to the base of the MN patch 102 by using suitable binder, such that the operator of the patch 102 may hold the handle 702 with his thumb and index finger to apply the patch to the skin to a desired target spot, followed by removing the handle 702 from the base of the patch 102 after successfully deploying the patch 102 on the skin surface with the MNs 104 penetrating the skin surface.

In addition, an animal experiment was conducted to evaluate the performance of the apparatus fabricated in accordance with embodiments of the present invention. The RFP-Hela loaded ice MNs can easily penetrate into mice skin by the thumb force. It is clear that there was no harm effects of ice MNs on mice skin as show in FIGS. 8A to 8D, except for the microholes created by the MNs. It was also observed that the holes gradually disappeared after 10 mins as shown in FIG. 8D.

Furthermore, the ice MNs may be applied in clinic applications. The inventors monitored the intensity red fluorescent protein secreted by the delivered RFP-Hela. It demonstrated that the RFP-Hela could survive in mice skin and continued to secrete RFP after being delivered into mice skin by ice MNs as shown in FIGS. 9A to 9C. Alternatively, the ice microneedles may be used for cell delivery.

These embodiments may be advantageous in that, the ice-based MNs may be used in various treatments of skin diseases and facelift by delivering all kinds of drugs and biologics. Example applications include the treatment such as (but not limited to) vitiligo, melanoma, skin regeneration, wound healing, hair regeneration, and anti-wrinkling.

Advantageously, the MN-based device may be applied for loading and transdermal delivery of various types of bioactive therapeutic agents (e.g. therapeutic cells, small molecular drug, proteins/peptides, DNA/RNA, bacteria, virus, fungi, et al.) in a minimally-invasive manner. This device can maintain the viability and bioactivity of loaded therapeutic agents. The device has enough mechanical strength, which ensures the device can penetrate across the stratum corneum and deliver the cargo into the targeted skin layers.

By selecting and loading certain therapeutic agents, the devices can be applied for different biomedical applications, such as cancer immunotherapy (by loading dendritic cells or T cells), treatment of vitiligo (by loading melanocytes), treatment of diabetes (by loading insulin or insulin-secreting cells), treatment of topical infection (by loading probiotic bacteria or bacteriophages) and promoting skin regeneration (by loading fibroblasts or stem cells).

Embodiments of the present invention may also provide the following advantages.

Firstly, the materials of present MNs are aqueous solutions which are readily accessible and easy to prepare. For example, the 2.5% wt DMSO in water or PBS and 200 mM sucrose dissolved in water or PBS. This is different from other MN devices usually made from polymer, metal, silicon and glass, which might involve with expensive raw materials, complex chemical synthesis and potential issue of biocompatibility.

Second, the fabrication process of the device is simpler, compared with the fabrication of solid or hollow MNs.

Third, this present invention integrates living cells into MNs as a ready-to-use device and the cells can maintain alive inside the device for a long-term storage. By harnessing the device according to the embodiments of the present invention, the transdermal delivery of cells can be easily performed without assistance of any extra device. Therefore, application processes can be greatly simplified. This is particularly different from other technologies or example devices for cell delivery which may involve complex and redundant procedures including cell harvest and preparation of cell infusing solution during each administration processes, or may require additional equipment for providing infusion pressure.

Forth, the microneedle patches can also be applied for loading and delivery of many types of bioactive therapeutics, such as drugs, protein/peptides, nucleic acid, virus and bacterial, et al, for different biomedical purposes, which is different from other examples that only focus on a single type of therapeutics.

In some embodiments, co-delivery of multiple types of therapeutics may be more preferable. The inventor devised that due to the presence of a large population of immune cells in the dermal layers of skin, MNs may be applied as an effective vaccination method because they can enhance the immunogenicity. For example, MNs may be used for localized delivery of immune checkpoint inhibitors such as aPD-1/PD-L1, which increases the therapeutic efficacy of Immune checkpoint blockade (ICB), and minimize the severe side effects.

Without wishing to be bound by theory, dendritic cells (DCs) are antigen-presenting cells and capable of activating antigen-specific T cells that thereby can recognize and eliminate tumor cells. The inventors devise that although DC vaccines have been demonstrated high safety and immunogenicity, clinical trials demonstrated limited clinical efficacy of DC vaccination. A possible reason is that the function and infiltration of activated T cells may be hampered by immunosuppressive microenvironment of tumors. An underlying mechanism of immunosuppression is the immune checkpoint, which is responsible for prevention of autoimmunity and maintenance of self-tolerance.

Preferably, immune checkpoint blockade (ICB) therapies using antibodies against programmed cell death protein 1 (anti-PD-1, aPD1), programmed death-ligand 1 (anti-PD-L1) and cytotoxic T-lymphocyte-associated protein (anti-CTLA-4) may be used to invigorating antitumor functions of T-cells. In some preferable embodiments of the present invention, DC vaccination in combination with ICB may be combined since DCs can foster activation of initial antigen-specific T-cells while immune checkpoint inhibitors can well-maintain antitumor functions of T-cells.

In some alternative examples, different types of MNs may be provided to encapsulate the aPD-1/PD-L1 for either monotherapy or combinational therapy. For example, hyaluronic acid MNs integrated with pH-sensitive dextran nanoparticles (NPs) that encapsulate aPD-1 and glucose oxidase (GOx), which achieved stimuli-responsive release of aPD-1 with tumor environment may be provided. Alternatively, a MN patch loaded with pH-responsive tumor-targeted lipid (NPs) to co-encapsulate aPD-1 and cisplatin for synergistic cancer immune-chemotherapy may be used.

In accordance with embodiments of the present invention, the microneedle patches, which may also refer as "cryomicroneedles" (cryoMNs) in this disclosure, are provided. In these preferred embodiments, living cells can be encapsulated inside cryoMNs and further delivered into skin after penetration of cryoMNs. By taking delivery of DC vaccines as a proof of concept, cryoMNs were demonstrate to greatly simplify the DC vaccination process by not only allowing easy performance of intradermal injection, but also achieving multiple injections with one donation, compared with traditional standard of care which generally involves cost and time-consuming procedure of repeated blood collections from patients with high batch-to-batch variation.

Preferably, the bioactive therapeutic agents in the microneedle device may further comprise antigen-presenting cells and at least one substance, such as an immune checkpoint inhibitor, arranged to boost the therapeutic effect of the antigen-presenting cells. For example, the immune checkpoint inhibitor includes antibodies against programmed cell death protein 1 (anti-PD-1), programmed death-ligand 1 (anti-PD-L1) or cytotoxic T-lymphocyte-associated protein (anti-CTLA-4), and the antigen-presenting cells include dendritic cells, such as antigen-pulsed dendritic cells, such that the microneedle device may be used to provide a therapeutic effect including activation of T-cells to enhance an antitumor immunity of the activated T-cells.

In this example embodiment, a stamp-like cryoMN patch co-encapsulated with antigen-pulsed DCs and aPD-1 for combinational cancer immunotherapy is provided. Referring to FIGS. 7A and 7B, a handle made of polylactic acid (PLA) may be fabricated by 3D printing technique and further integrated/attached with the cryoMNs, which greatly facilitates the manipulation and skin penetration of the cryoMNs.

With reference also to FIGS. 10A to 13F, experiments have been performed to evaluate the performance of the cryoMN patch. It was observed that, DCs could maintain alive in cryoMNs and interdermally injected into skin. The results also show that vaccination with cryoMNs co-encapsulated with antigen-pulsed DCs and aPD-1 (cryoMNs@DCs&aPD-1) could promote activation and drainage of DCs to lymph nodes, further inducing potent cellular immuno responses. In addition, vaccination with cryoMNs@DCs&aPD-1 enhanced the antitumor immunity of T-cells and increased infiltration of activated CD8+ effector T-cells in the tumor, resulting in stronger antitumor immunotherapy efficacy in the both prophylactic and therapeutic tumor models, compared with the vaccinations with cryoMNs@DCs or cryoMNs@aPD-1.

In the experiment, stainless steel master mold of MNs (10×10 array, 300 μm base diameter, 700 μm pitch, 5 μm tip radius, and 1200 μm height) was purchased from Micropoint Technologies Pte Ltd (Singapore). Sylgard® 184 silicone elastomer kit was purchased from Dow Corning (USA). Dimethyl sulfoxide (DMSO), Poly(vinyl alcohol) (PVA), phosphate buffered saline (PBS), sucrose, bovine serum albumin (BSA), cell strainer (100 μm), ovalbumin (from chicken egg white, OVA), and lipopolysaccharides (from *Escherichia coli* 0111:B4, LPS) were purchased from Sigma-Aldrich (USA). DMEM, RPMI-1640, fetal bovine serum (FBS), 10000 U/mL penicillin-streptomycin (P/S), trypsin-EDTA, alamarBlue™ Cell Viability Reagent, LIVE/DEAD™ viability/cytotoxicity kit, 2-Mercaptoethanol, MEM non-essential amino acids solution, sodium pyruvate, HEPES, ACK Lysing Buffer, anti-mouse MHC Class II (APC, clone AF6-120.1) and CD86 antibody (APC, clone GL1), CyQUANTT™ LDH Cytotoxicity Assay were purchased from ThermoFisher Scientific (USA). Mouse IFN-γ ELISA Kit were purchased from the StemCell Pte. Ltd. (Singapore). Recombinant murine granulocyte-macrophage colony stimulating factor (GM-CSF) was purchased from R&D Systems (USA). Recombinant murine IL-4 was purchased from Peprotech (USA). H&E Stain Kit (Hematoxylin and Eosin, ab245880) was purchased from Abcam (USA). Anti-mouse CD8a (FITC, clone 53-6.7), CD4 (APC, clone RM4-5), CD279 (aPD-1) (Ultra-LEAF™ Purified, clone RMP1-14), CD279 (FITC, clone 29F.1A12), FOXP3 (PE, clone MF-14), INF-γ (PE, clone XMG1.2), CD3 (PE, clone 17A2) and CD11c (FITC, clone N418) antibodies were purchased from BioLegend (USA).

Female C57BL/6 mice (6 to 8 weeks) were purchased from Laboratory Animal Research Unit (LARU). Animal experiments were performed in accordance with ethical approval by Animal Research Ethics Sub-Committee of City University of Hong Kong, under the Internal Ref: A-0493. The B16 melanoma cell line transfected with ovalbumin (B16-OVA) was gifted by the lab of Professor Jiandong Huang from School of Biomedical Sciences, The University of Hong Kong, Hong Kong. B16-OVA cells were cultured in DMEM supplemented with 10% FBS and 1% P/S in culture dish at 37° C. and 5% $CO_2$. The culture medium was changed every 2 or 3 days and culture dish with 80 ~ 90% confluence were used for further cell experiments.

Bone marrow-derived DCs were isolated and generated from femur bones of C57BL/6 mice according to previous study. The detail protocol is shown in Supporting Information. To prepare the OVA pulsed DCs (OVA-DCs), DCs were incubated with 50 μg/mL OVA for 24 h.

The Fabrication of DCs and aPD-1 co-encapsulated stamp-like cryoMN patch is similar to the process described earlier referring to FIG. 2. In this example, PDMS MN mold was obtained by replication of the stainless steel master mold according to the previous studies, then treated with $O_2$ plasma and sterilized by 20 min UV exposure. 200 μL PVA (5 wt %) was cast into PDMS mold and then the handle was vertically incubated in PVA solution as shown in FIG. 1. After freezing under −80° C. refrigerator for 20 min, the handle integrated with PVA base was demoulding and transformed in −20° C. Herein, PBS supplemented with 2% (v/v) DMSO and 100 mM sucrose was used as cryogenic medium. 50 μL cryogenic medium supplemented with 1 μg/μL aPD-1 was casted into mold and centrifuged at 3,000 rpm for 3 min. Then, 50 μL cryogenic medium with 1 μg/μL aPD-1 and 1×10⁵ OVA-DCs was casted into the same mold and centrifuged at 500 rpm for 1 min to allow the cells fill up the cavities of MNs. Next, the mold was put in 4° C. for 30 min and then transferred in −20° C. The prepared the handle with PVA base was gently touched with the cryogenic medium in the mold. After freezing in −20° C. for 4 h and −80° C. for overnight, the stamp-like cryoMN patch was obtained after demoulding. The patch was either stored under −80° C. or liquid nitrogen before using.

Referring to FIG. 10A to FIG. 13F, there is shown experimental results of the stamp-like cryoMN patch fabricated in accordance with embodiments of the present invention.

In an experiment to test in vivo immune responses after vaccination with stamp-like cryoMN patch, C57BL/6 mice were randomly divided into five groups (n=5): untreated, cryoMNs, cryoMNs@DCs, cryoMNs@aPD-1 and cryoMNs@DCs&aPD-1. Each of mice from treatment groups receive vaccination with 4 patches of cryoMNs, cryoMNs@DCs, cryoMNs@aPD-1 or cryoMNs@DCs&aPD-1 on day 0, 3 and 6. Draining lymph nodes (dLN) and spleens of mice were harvested 3 days after last vaccination, cut into small pieces and homogenized by grinding with the end of a sterile syringe and processed into a single cell suspension. Cells were stained with fluorescence-labeled antibodies. The stained cells were measured by flow cytometer (BD Biosciences) and were analyzed by FlowJo software (TreeStar).

Splenocytes (5×10⁵ per well) were seeded in the 96-well plate and re-stimulated with 50 μg/ml OVA for 2 days. The production of IFN-γ in culture supernatants was measured by mouse IFN-γ ELISA Kit. The cytotoxicity T lymphocyte (CTL) assay was conducted following the manufacturer's protocol (CyQUANT™ LDH Cytotoxicity Assay Kit). Splenocytes (effector cells) and B16-OVA (target cells) were then co-cultured in U-bottomed 96-well plates with the cell number ratios of 100:1. After incubation for 2 h at 37° C., the lysed target cells were quantified.

In an experiment to test in vivo tumor models and antitumor effect, in the therapeutic model, 2×10⁵ B16-OVA cells were inoculated subcutaneously into the right flanks of C57BL/6 mice on the right flank. After XX days, the melanoma-bearing mice were randomly divided into four groups (n=5): untreated, cryoMNs@DCs, cryoMNs@aPD-1 and cryoMNs@DCs&aPD-1. Each of mice from treatment groups receive vaccination with 4 patches of cryoMNs@DCs, cryoMNs@aPD-1 or cryoMNs@DCs&aPD-1 on day 1, 4 and 7. In the prophylactic model, C57BL/6 mice received vaccination according to on day 0, 3 and 6. On day 9, the 2×10⁵ B16-OVA cells were inoculated subcutaneously into the right flanks of C57BL/6 mice on the right flank. Once the tumor became palpable, the tumor volume was measured with a digital caliper and was calculated according to the following formula: width 2×length×0.5. The tumors were harvested for taking images and then processed into a single cell suspension for staining.

Cells were stained with fluorescence-labeled antibodies. The stained cells were measured by flow cytometer (BD Biosciences) and were analyzed by FlowJo software (TreeStar). For DC infiltration and maturation test, the cells were stained with anti-CD11c, anti-CD86 and anti-MHCII antibodies. For T-cell analysis, the cells were stained with anti-CD3, anti-CD8a, anti-CD4, anti-Foxpγ and anti-IFN-γ antibodies. All antibodies were used following the manufacturers' instructions.

Quantitative data are represented as means±standard deviations (SD). Statistical analysis was performed by using Student's t test or one-way analysis of variance (ANOVA). Probability (p) values less than 0.05 were considered statistically significant.

It will be appreciated by persons skilled in the art that numerous variations and/or modifications may be made to the present invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A cryo formulation-based microneedle device for transdermal delivery of bioactive therapeutic agents, comprising:
    one or more microneedle patches each including an array of miniaturized needles, each miniaturized needle defining a base end and a tip; and
    a substrate to which the base end of the array of miniaturized needles is attached or integrated thereto;
    wherein the microneedle patches are in a cryo status;
    wherein each of the one or more microneedle patches are adapted to be applied on a skin surface, in which the miniaturized needles penetrate into skin;
    wherein the one or more microneedle patches consist of a matrix solution and a plurality of biological cells as the one or more bioactive therapeutic agent;
    wherein the miniaturized needles are further arranged to melt so as to release one or more bioactive therapeutic agents into the skin to achieve a targeted therapeutic effect; and
    wherein the matrix solution consists of water and a cryoprotectant, the cryoprotectant comprises 2.5% wt of dimethyl sulfoxide (DMSO) and 100 to 200 mM sucrose.

2. The microneedle device according to claim 1, wherein the plurality of biological cells including at least one of cancer cells, fibroblasts, endothelial cells, smooth muscle cells, stem cells, melanocytes, dendritic cells, neutrophils, and T-cells.

3. The microneedle device according to claim 1, wherein the therapeutic agents plurality of biological cells comprise antigen-presenting cells and at least one substance arranged to boost the therapeutic effect of the antigen-presenting cells.

4. The microneedle device according to claim 3, wherein the at least one substance includes an immune checkpoint inhibitor.

5. The microneedle device accordance to claim 4, wherein the immune checkpoint inhibitor includes antibodies against programmed cell death protein 1 (anti-PD-1), programmed death-ligand 1 (anti-PD-L1) or cytotoxic T-lymphocyte-associated protein (anti-CTLA-4).

6. The microneedle device according to claim 3, wherein the antigen-presenting cells include dendritic cells.

7. The microneedle device according to claim 6, wherein the antigen-presenting cells include antigen-pulsed dendritic cells.

8. The microneedle device according to claim 3, wherein the therapeutic effect includes activation of T-cells to enhance an antitumor immunity of the activated T-cells.

9. A method of fabricating a microneedle device in accordance with claim 1, comprising the steps of:
    casting the matrix solution containing the bioactive therapeutic agents into a mold defined with an array of microneedle structures;
    freezing the solution to define the array of microneedle structures on one of the one or more microneedle patches; and
    detaching the one or more microneedle patches from the mold.

10. The method according to claim 9, wherein the mold includes a PDMS mold or a metal mold.

11. The method according to claim 9, further comprising the step of urging the matrix solution into the array of microneedle structures defined on the mold.

12. The method according to claim 11, wherein the matrix solution is urged into the mold using centrifugation.

13. A method of using the microneedle device in accordance with claim 1, comprising the step of:
    removing the microneedle device from a storage place; and
    applying the microneedle device within a predetermined period of time after removal from the storage place.

14. The method of claim 13, wherein the predetermined period of time is 1-30 seconds.

15. The method of claim 13, wherein the one or more microneedle patches are arranged to facilitate a predetermined penetration depth of the one or more bioactive therapeutic agents into the skin.

16. The method of claim 15, wherein the predetermined penetration depth is 50-1000 μm.

17. The method of claim 13, further comprising the step of temporally attaching the microneedle device to a handle, thereby allowing an operator to apply the microneedle device by holding the handle.

* * * * *